US008828409B2

(12) United States Patent
Rhee et al.

(10) Patent No.: US 8,828,409 B2
(45) Date of Patent: Sep. 9, 2014

(54) **VACCINE COMPRISING RECOMBINANT CLPP PROTEIN OF *STREPTOCOCCUS PNEUMONIAE***

(75) Inventors: Dong-Kwon Rhee, Gyeonggi-do (KR); Hyeok-Young Kwon, Gyeonggi-do (KR); Mu-Hyeon Choi, Chungcheongnam-do (KR); Abiodun David Ogunniyi, Manningham (AU); James Cleland Paton, Parkside (AU)

(73) Assignees: Sungkyunkwan University, Seoul (KR); Adelaide Research & Innovation Pty Ltd., Adelaide (AU)

( * ) Notice: Subject to any disclaimer, the term of this patent is extended or adjusted under 35 U.S.C. 154(b) by 764 days.

(21) Appl. No.: 12/953,677

(22) Filed: Nov. 24, 2010

(65) Prior Publication Data

US 2011/0129501 A1 Jun. 2, 2011

Related U.S. Application Data

(62) Division of application No. 10/554,760, filed on Aug. 12, 2008, now abandoned.

(51) Int. Cl.
*A61K 39/09* (2006.01)
*C12P 21/06* (2006.01)
*A61K 39/00* (2006.01)

(52) U.S. Cl.
CPC ......... *A61K 39/092* (2013.01); *A61K 2039/522* (2013.01); *A61K 2039/55505* (2013.01); *A61K 2039/55566* (2013.01)
USPC ...................................... 424/244.1; 435/69.1

(58) Field of Classification Search
None
See application file for complete search history.

(56) References Cited

U.S. PATENT DOCUMENTS 6,685,943 B1 2/2004 Hook et al.

FOREIGN PATENT DOCUMENTS

WO 9935270 7/1999

OTHER PUBLICATIONS

Nair et al Microbiology (2003), 149, 407-417.
Kwon et al, Infection and Immunity, Jul. 2003, vol. 71, p. 3757-3765.
Kwon et al, Infection and Immunity, Oct. 2004, p. 5646-5653, vol. 72, No. 10.
Li et al, The Journal of Immunology, 2007, 178: 5271-5276.
Japanese Patent Office, Office Action for Japanese Patent Application No. 2005-512815 dated Feb. 24, 2010 and English language translation.
NCBI Sequence; Accession No. AE008443; *Streptococcus pneumoniae* R6 section 59 of 184 of the complete genome; Jul. 24, 2007; pp. 1-8.
Novagen; pET-30a-c(+) Vectors; TB095 Dec. 1998; 2 pages.
Chastanet et al.; "Regulation of *Streptococcus pneumoniae* clp Genes and Their Role in Competence Development and Stress Survival"; Journal of Bacteriology, Dec. 2001, vol. 183, No. 24; pp. 7295-7307.
Robertson et al.; "Essentiality of clpX, but Not clpP, clpL, clpC, or clpE, in *Streptococcus pneumoniae* R6"; Journal of Bacteriology, May 2003, vol. 185, No. 9; pp. 2961-2966.
Robertson et al.; "Global Transciptional Analysis of clpP Mutations of Type 2 *Streptococcus pneumoniae* and Their Effects on Physiology and Virulence"; Journal of Bacteriology, Jul. 2002, vol. 184, No. 13; pp. 3508-3520.
Korean Patent Office, Office Action for Korean Patent Application No. 10-2006-7011120 (Sep. 30, 2007).
PCT/KR2003/002929; International Search Report dated Oct. 26, 2004.

*Primary Examiner* — Padma V Baskar
(74) *Attorney, Agent, or Firm* — Renner, Otto, Boisselle & Sklar, LLP

(57) ABSTRACT

A method for immunizing a human or animal against pneumococcal infections, comprising by administering a vaccine comprising a purified recombinant caseinolytic protease P (ClpP) protein of *S. pneumoniae* in an immunologically effective amount to the human or animal.

1 Claim, 19 Drawing Sheets

VACCINE COMPRISING RECOMBINANT CLPP PROTEIN OF *STREPTOCOCCUS PNEUMONIAE*

CROSS-REFERENCE TO RELATED APPLICATION

The present application is a divisional of and claims priority under 35 U.S.C. §120 to copending, commonly assigned U.S. application Ser. No. 10/554,760, filed 28 Oct. 2005, for which all requirements under 35 USC 371 were completed on 12 Aug. 2008, now abandoned, the entirety of which is hereby incorporated herein by reference.

TECHNICAL FIELD

This invention relates to a vaccine comprising a recombinant ClpP (Caseinolytic pretease P) protein of *Streptococcus pneumoniae* as an antigen. A relevant section of *S. pneumoniae* is shown in the appended Sequence Listing, including SEQ ID NOS. 1 and 2. SEQ ID NO. 1 shows the full sequence of GenBank AE008443, i.e., section 59 of 184 of the complete qenome of *S. pneumoniae* while SEQ ID NO. 2 shows only base sequences 5416 to 6006 of said section 59 of 184 of the complete genome of *S. pneumoniae.*

BACKGROUND

*Streptococcus pneumoniae*, a gram-positive and naturally transformable organism, causes various infections in human and animal such as bacterial pneumonia, otitis media and meningitis (Willett, H. P. 1992. *Streptococcus pneumoniae*. In *Zinsser Microbiology*. Joklik, W. K., Willet, H. P., Amos, D. B. and Wilfert, C. M., (eds). Prentice-Hall International, London, pp. 432-442). It is known that appearance of multi-drug resistant bacteria makes it difficult to treat infections caused by *Streptococcus pneumoniae* using antibiotics. 23-valent polysaccharide vaccines (Pneumovax 23 (Merck) and Pnu-Imune 23 (Wyeth-Lederle)), which comprise capsular polysaccharides (CPS) as an effective antigen, are commercially available to prevent pneumococcal infections. However, these vaccines have disadvantages in that they were not effective due to low antibody production rate when given to infants and young children, and in that they have no memory response. 7-valent conjugate vaccine (Prevnar (Wyeth-Lederle)), which is made by conjugating 7 types of CPS to a carrier protein, has been developed to solve the disadvantages of 23-valent vaccines as mentioned above. However, this vaccine is very restrictly applied as a vaccine to prevent pneumoccocal infections, since it is very expensive and has protective effect against only 7 types among 95 types or more of the pneumococcus. Therefore, there have been attempts to develop a vaccine with a protein having high antigenicity to prevent pneumococcal infections. Pneumolysin (Ply) toxoid is known as a virulence factor of the pneumococcus that binds to cholesterol of host cell to form pore in the cell, and thus there have been attempts to develop vaccines using an attenuated pneumolysin (PdB). However, pneumolysin has a very high in vivo and in vitro toxicity. Also, the PdB was not effective when given alone, and elicited increased survival rate against the pneumoccocal infections only when given in combination with other virulence factors such as Pneumococcal Surface Protein A (PspA), Choline Binding Protein (CbpA), Pneumococcal Surface Adhesin A (PsaA), LytA (Ogunniyi, A. D. et al., 2000, Immunization of mice with combinations of pneumococcal virulence proteins elicits enhanced protection against challenge with *Streptococcus pneumoniae*. Infect. Immun. 68:3028-3033). Thus, since candidate antigen proteins in conventional vaccines for prevention of pneumoccocal infections have low antigenicity or have no protective effects against all serotypes of the pneumococcus, there remains a need to develop attenuated vaccines as well as candidate antigen proteins which have high immunogenicity and are conservatively present in all types of the pneumococcus.

The pneumococcus is carried in the nasopharynx of healthy individuals, and this is a major reservoir for pneumococcal infections. Pneumococci are subject to a number of environmental stresses in vivo. Change of environmental niche in the host, such as penetration of pneumococci from the nasopharynx into the bloodstream, can trigger dramatic changes in morphology as well as gene expression. For example, pneumococci in the nasopharynx have been shown to be predominantly of a transparent colony phenotype and tend to express less capsule and more choline binding protein A (CbpA), whereas pneumococci in the bloodstream are predominantly of the opaque colony morphology and tend to produce more capsule and less CbpA (Kim, J. O. et al., 1998. Association of intrastrain phase variation in quantity of capsular polysaccharide and teichoic acid with the virulence of *Streptococcus pneumoniae*. J. Infect. Dis. 177:368-377). Furthermore, *S. pneumoniae* encounters heat stress during its pathogenic course after penetration from the nasal mucosa (30 to 34° C.) (Lindemann, J. et al., 2002, Nasal mucosal temperature during respiration. Clin. Otolaryngol. 27:135-139) into blood and/or meninges (37° C.). This temperature shift may serve as a key trigger for a rapid, transient increase in synthesis of a highly conserved set of proteins referred to as heat-shock proteins (HSPs) (Neidhardt, F. C. et al., and R. A. VanBogelen. 1987. Heat shock response, p. 1334-11345. In F. C. Neidhardt, J. L. Ingraham, K. B. Low, B. Magasanik, M. Schaechter, and H. E. Umbarger (ed.), *E. coli* and *Salmonella typhimurium*: Cellular and molecular biology. ASM Press, Washington, D.C). HSPs protect bacteria against such adverse effects as elevated temperatures, exposure to ethanol, oxidative stresses, or heavy metals thus increasing their survival rate. Therefore, a thorough understanding of the heat shock response could provide useful information on adaptation of the pneumococcus to the hostile environment it encounters.

HSPs can be classified into Hsp100, Hsp70, Hsp60, and small Hsp families depending on molecular weight, and are ubiquitously present in prokaryotes and eukaryotes. One of the HSPs, hsp100/Clp (caseinolytic protease) family, is present as a 104-kDa protein in eukaryotes, but as an 80-95-kDa protein in prokaryotes. It carries out a chaperone function and is also involved in proteolysis thereby removing damaged and denatured proteins. Proteolysis by Clp requires a serine-type peptidase ClpP subunit and a regulatory ATPase subunit (Schirmer, E. C., et al., 1996. HSP100/Clp proteins: a common mechanism explains diverse functions. Trends Biochem. Sci. 21:289-296). Regulatory Clp subunit proteins can be assigned, in general, to two classes: class I, which comprises clpA, B, C, and D, contains two ATP-binding regions; class II, which comprises clpM, N, X, and Y, contains only one ATP-binding region. Clps have been classified by the size of the central spacer segment, the need for gaps in aligning the overall sequences, and sequence similarities in the well-conserved regions, and in the N- and C-terminal segments, the variable leader regions have very different sequences in each subfamily (Supra, Schirmer, E. C., et al., 1996).

Although substantial progress has been made on understanding the mechanisms of action of the Clp family in Gram-negative bacteria such as *E. coli*, little is known about Clp in Gram-positive bacteria. The clpP gene and clpC operon are negatively regulated by CtsR, which recognizes a directly repeated operator sequence (A/GGT CAA ANA NA/GG TCA AA), but clpX does not have this sequence and their specific mechanisms of action have not been determined in detail (Derre, I., et al., 2000. The CtsR regulator of stress response is active as a dimer and specifically degraded in vivo at 37° C. Mol. Microbiol. 38:335-347).

Since a variety of environmental signals including temperature and nutrient availability can control the expression of virulence factors, we previously examined the protein profiles of the heat shock response in pneumococci after exposure of the cells to several stresses. The major proteins induced by heat shock were 62-, 72-, and 84-kDa in size, identified subsequently as GroEL, DnaK, and ClpL, respectively. However, pulse-labeling of proteins with [$^{35}$S]-methionine revealed that certain conditions which are known to induce stress responses in *E. coli* and *B. subtilis* failed to induce any high molecular weight HSPs such as GroEL and DnaK homologues. However, a temperature shift from 30 to 37° C. in vitro, similar to that encountered by *S. pneumoniae* after translocation from the nasal mucosa to the lungs, triggered induction of DnaK and GroEL (Choi, I. H., et al., 1999. Limited stress response in *Streptococcus pneumoniae*. Microbiol. Immunol. 43: 807-812). The nucleotide sequences of ClpL from several Gram-positive organisms are known (*L. lactis* [X62333]; *S. aureus* [AP003365, AP003137]; *S. pyogenes* [AE006538, AE004092]; *Lactobacillus rhamnosus* [AF323526]), but functional studies on ClpL have been limited. Recently in *S. pneumoniae*, the clpP$^-$ mutant was sensitive to high temperature, $H_2O_2$ and puromycin, and attenuated virulence significantly (Robertson, G. T., et al., 2002. Global transcriptional analysis of clpP mutations of type 2 *Streptococcus pneumoniae* and their effects on physiology and virulence. J. Bacteriol. 184:3508-3520). Specific roles of other heat shock genes, clpC, clpE, and clpX have not been fully elucidated (Charpentier, E. et al., 2000. Regulation of growth inhibition at high temperature, autolysis, transformation and adherence in *Streptococcus pneumoniae* by clpC. Mol Microbiol 37:717-726; Chastanet, A., et al., 2001. Regulation of *Streptococcus pneumoniae* clp genes and their role in competence development and stress survival. J. Bacteriol. 183:7295-7307).

Accordingly, in order to develop antigen proteins which are present universely in all types of the pneumococcus, and vaccines using the same, we investigated the effect of heat shock on ClpL and ClpP synthesis and evaluated the impact of clpL$^-$ and clpP$^-$ mutation on in vitro expression of key pneumococcal virulence genes. Furthermore, the effect of clpL$^-$ and clpP$^-$ mutation on the virulence of *S. pneumoniae* was evaluated in a mouse intraperitoneal challenge model. Here we demonstrate that the heat shock process induced expression of pneumolysin (Ply) and modulated the expression of other virulence factors in wild-type pneumococci. We also show that clpP$^-$ mutation resulted in an increase in mRNA expression, but not in the activity of Ply at elevated temperatures. Subsequently, we investigated further the underlying mechanism by which ClpP attenuates virulence and determined whether ClpP immunization could protect the mice against the challenge with virulent *S. peumoniae*, thereby we completed this invention.

DETAILED DESCRIPTIONS OF THE INVENTION

It is an object of this invention to provide a vaccine comprising a recombinant ClpP protein derived from *S. pneumoniae* as an antigen.

It is another object of this invention to provide a process for preparing a recombinant ClpP protein of *S. pneumoniae* for use in a vaccine.

It is a further object of this invention to provide a method for immunizing a human or animal against the pneumococcal infections, comprising by administering a vaccine comprising a ClpP protein of *S. pneumoniae* in an immunologically effective amount to the human or animal.

It is another object of this invention to provide a mutant of *S. pneumoniae* as a live attenuated vaccine.

For the above mentioned objects, in an embodiment of this invention, we investigated the effect of heat shock on ClpL and ClpP synthesis and evaluated the impact of clpL$^-$ and clpP$^-$ mutation on in vitro expression of key pneumococcal virulence genes. In another embodiment of this invention, the effect of clpL$^-$ and clpP$^-$ mutation on the virulence of *S. pneumoniae* was evaluated in a mouse intraperitoneal challenge model, and it was demonstrated that the heat shock process induced expression of pneumolysin (Ply) and modulated the expression of other virulence factors in wild-type pneumococci. In a further embodiment of this invention, we also show that clpP$^-$ mutation resulted in an increase in mRNA expression, but not in the activity of Ply at elevated temperatures. Further, in another embodiment of this invention, we investigated further the underlying mechanism by which ClpP attenuates virulence and showed that ClpP immunization could protect the mice against the challenge with virulent *S. pneumoniae.*

According to our studies, after heat shock, an increase in pneumolysin mRNA expression was demonstrated in the ClpP$^-$ mutant, whereas the level and haemolytic activity of pnemolysin revealed no increase. Mice challenged with ClpP$^-$ mutant showed a significant increase in survival time and rate as compared with mice challenged with wild type, which demonstrates an attenuation in virulence of ClpP$^-$ mutant. This suggests that ClpP$^-$ mutant may be potentially used as an attenuated vaccine. Also, the biochemical fractionation study of *S. pneumoniae* shows that the ClpP transports from cytoplasm to cell wall after heat shock, thus suggesting that when the pneumococcus causes a host to infect, the stress it encounters within the host cell, can expose ClpP to the host cell. In addition, in the experiments to determine whether ClpP can provide immunoprotection against the pneumococcal infection, Malb/c mice were injected intraperitoneally with three doses of 10 μg of ClpP protein at 2-week intervals, then the mice were challenged intraperitoneally with $1\times10^5$ CFU of a highly virulent *S. pneumoniae* D39 strain (type 2), followed by determining the survival time of each mouse. The results show that the survival time for mice immunized with ClpP is comprable to that for the group that received attenuated pneumolysin (PdB), suggesting that ClpP is exposed outside of the pneumococcus by the stress which the pneumococcus encounters in host cells, thus functions as an antigen as well as has protective activity against the pneumococcal infection comparable to that of attenuated pneumolysin. Thus, according to this invention, ClpP protein can be used as an effective vaccine against the pneumococcal infection.

ClpP protein of *S. pneumoniae* of this invention is serine protease having 21 kDa of molecular weight (Genebank AE008443, for which section 59 of 184 of the complete genome is shown in appended SEQ ID NO. 1) which is one of heat shock proteins. In this invention, recombinant ClpP protein can be prepared by large scale expression and isolation in accordance with conventional genetic engineering techniques in the art. Briefly, ClpP protein can be prepared by a method comprising by cloning ORF (open reading frame) (base sequences 5416 to 6006, Genebank AE008443, for which said base sequences 5416 to 6006 of section 59 of 184 of the complete genome are shown in appended SEQ ID NO. 2) of ClpP gene into expression vector such as pET30(a) (Novagen) to form plasmid pET30(a)-ClpP (FIG. 1), introducing the plasmid into a host cell such as animal cells, plant cells, or *E. coli* to express the ClpP protein, and purifying the protein. Expression vectors, hosts, culturing conditions, gene insertion techniques etc. can be appropriately selected within ordinary knowledge of those skilled in the art. An embodiment of this invention relates to a preparation of recombinant ClpP proten using *E. coli*. ClpP protein is related to modulating the expression of virulence factors of the *Streptococcus pneumoniae* such as pneumolysin, PsaA, CbpA, PspA, at the level of mRNA and protein.

The vaccine according to this invention may be administered by various route, including parenterally, intradermally, transdermally (by using a sustained release polymer), intramuscularly, intraperitoneally, subcutaneously, orally, and intranasally. The vaccine is administered in an immunologically effective amount. An immunologically effective amount is defined as a dose suitable for inducing immune response. The dose can vary depending on various factors such as age, body weight and physical state of animal or human subject to be immunized, ability of immunity system in animal to produce antibodies, and the extent of desired protection. A person skilled in the art can easily determine the effective amount through a routine way for generating a dose-response curve. Immunization may be achieved by administering a single dose of vaccine, or may require the administration of several booster doses. The dose of ClpP will typically range from 1 μg to 50 μg, or more or less, if appropriate. The vaccine according to this invention may be formulated by adding ClpP protein to an immunologically acceptable diluent or carrier in a conventional manner. Diluents or carriers include, but are not limited to, water, brine, dextrose or glycerol. Also, pH stabilizers, isotonizing agents, wetting agents, or emulsifiers may be added to the vaccine. In addition, the vaccine may further comprise other pharmaceutically acceptable adjuvants such as aluminum hydroxide, alum, QS-21, monophosphoryl lipid A, and 3-O-deacylated monophosphoryl lipid A (3D-MPL). The vaccine may be typically formulated in injectable dosage forms, in a solution or suspension form, or in a solid form which can be solublized or suspended prior to use. Further, the vaccine may be formulated in an intranasal or oral preparation in the conventional manner in the art. The intranasal preparations may include excipients, which do not make an irritation on nasal mucosa, or do not inhibit severely the mucociliary function, and diluents such as water, brine. The intranasal preparations may include preservatives such as chlorobutanol and benzalkonium chloride, and also include sufactants for enhancing the absorption of protein antigen by nasal mucosa. Oral liquid preparations may be, for example, in the form of aqueous or oily suspension, solution, emulsion, syrup, or elixir, or may be present in dry state such as in the form of tablet for reconstitution with water or other suitable diluents prior to use. Solutions may contain conventional additives such as suspending agents, emulsifying agents, non-aqueous diluents (may include edible oils), or preservatives. In order to make a vaccine preparation, purified ClpP protein can be lyophilized and stabilized.

Figure 1:
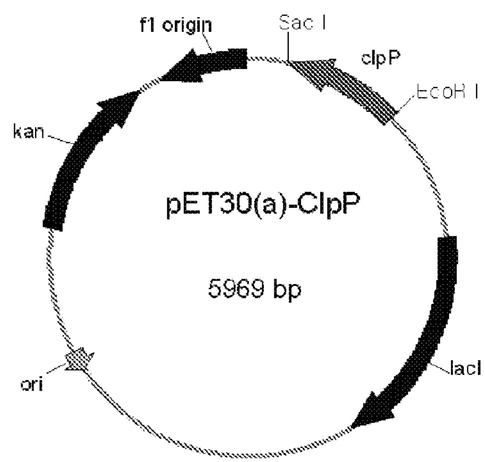
FIG. 1 shows a structure of pET30(a)-ClpP expression vector.

Hereinafter, this invention will be described in more detail by way of the examples. The following examples are presented only to illustrate this invention, but are not intended to limit the scope of the invention. In addition, the references, which are described herein, are incorporated herein by reference.

EXAMPLE

Example 1

Effect of Heat Shock and Mutations in ClpL and ClpP on Virulence Gene Expression in *Streptococcus pneumoniae*

In Example 1, the effect of heat shock on ClpL and ClpP synthesis was investigated and the impact of clpL$^-$ and clpP$^-$ mutation on in vitro expression of key pneumococcal virulence genes was evaluated. In addition, the effect of clpL$^-$ and clpP⁻ mutation on the virulence of *S. pneumoniae* was evaluated in a mouse intraperitoneal challenge model.

1. Materials and Methods i) Bacterial Strains, Growth Conditions, and Transformation.

The bacterial strains used in this work are presented in Table 1. *S. pneumoniae* CP1200 (Supra, Choi, I. H. et al., 1999), a derivative of Rx-1 (non-pathogenic *S. pneumoniae* having no capsule) was used in this study and was grown at 37° C. in Casitone-Tryptone (CAT) based medium to mid-exponential-phase: 1 L of CAT based medium (Difco Laboratories, USA) contained 10 g of enzymatic casein hydrolysate, 5 g of tryptophan (Difco Laboratories), 1 g of yeast extract (Difco Laboratories), 5 g of NaCl, 5 mg of choline (Sigma, USA), 0.2% glucose (Sigma, USA), 16.6 mM dipotassium phosphated (Sigma, USA). Complete transformation medium was prepared from CAT broth by addition of (per liter): 147 mg of $CaCl_2$ and 2 g of bovine serum albumin (fraction V; Sigma). Competence was controlled by appropriate addition of the competence specific peptide and quantitated as novobiocin-resistant transformants obtained after exposure of cells to DNA in culture medium as described previously (Havarstein, L. S., et al., 1995. An unmodified heptadecapeptide pheromone induces competence for genetic transformation in *Streptococcus pneumoniae*. Proc. Natl. Acad. Sci. U.S.A. 92:11140-11144). Encapsulated strain D39 (type 2) was grown in brain heart infusion broth (Difco Laboratories, USA) or Todd Hewitt broth (Difco Laboratories, USA) and transformed as previously described (Bricker, A. L., et al., 1999. Transformation of a type 4 encapsulated strain of *Streptococcus pneumoniae*. FEMS Microbiol. Lett. 172:131-135). For selection of pneumococcal transformants, erythromycin or novobiocin was added to growth medium at a concentration of 2.5 μg/ml or 10 μg/ml, respectively. *Escherichia coli* strains (BL21(DE3), DH5α, XL1-Blue listed in Table 1) were grown in Luria-Bertani (LB) broth or on LB agar. Plasmids were introduced into *E. coli* by transformation as previously described (Hanahan, D. et al., 1983. Studies on transformation of *Escherichia coli* with plasmids. J. Mol. Biol. 166:557-580). For selection of *E. coli* transformants, ampicillin (100 μg/ml) was added to the growth medium. Plasmid vectors along with new transformants generated in this study are listed in Table 1.

TABLE 1

Bacterial strains and plasmids used in Example 1.

| Strain or plasmid | Relevant characteristics | Reference or source |
|---|---|---|
| *E. coli* strains | | |
| BL21(DE3) | gal (λcIts857 ind1 Sam7 nin5 lacUV5-T7 gene1) | Novagen |
| DH5α | SupE44 ΔlacU169 (ø80 lacZΔM15) | Supra, Hanahan et al, 1983 |
| XL1-Blue | RelA1 lac [F' proAB lacI$^q$Z ΔM15 Tn10(Tet$^r$)] | Stratagene |
| *S. pneumoniae* strains | | |
| CP1200 | Nonencapsulated derivative of Rx1, malM511 str-1 | Morrison et al., 1983* |
| HYK1 | CP1200, Δ clpL::ermB | Infra, Kwon et al., 2003 |
| HYK2 | CP1200, Δ clpP::ermB | Infra, Kwon et al., 2003 |
| D39 | Encapsulated, type 2 | Infra, Avery et al., 1944 |
| HYK302 | D39, Δ clpP::ermB | Infra, Kwon et al., 2003 |
| HYK304 | D39, Δ clpL::ermB | Infra, Kwon et al., 2003 |
| Plasmids | | |
| pET30 (a) | 5.4-kb, Ap$^r$ | Novagen |
| PBluescript | 3.0-kb, Ap$^r$ | Stratagene |
| PGEM-T | 3.0-kb, Ap$^r$, TA cloning vector | Promega |
| pG8413 | 1.3-kb, clpL PCR fragment in pBluescript | Infra, Kwon et al., 2003 |
| pKHY004 | 7.5-kb, Histidine tagged clpL in pET30(a) | Infra, Kwon et al., 2003 |

*Morrison, D. A. et al., 1983, Isolation and characterization of three new classes of transformation-deficient mutants of *Streptococcus pneumoniae* that are defective in DNA transport and genetic recombination. J. Bacteriol. 156(1):281-290.

ii) Preparation of Antisera.

Production of HSP antibodies against *S. pneumoniae* DnaK and GroEL has been described previously (Supra, Choi et al., 1999). To prepare antibodies against ClpL and ClpP, an exponential culture of *S. pneumoniae* CP1200 was incubated at 42° C. for 30 min; the cells were sonicated and proteins were separated by sodium dodecyl sulfate 10% polyacrylamide gel electrophoresis (SDS-PAGE) and lightly stained with Coomassie brilliant blue. The 84- and 21-kDa protein bands were cut out and electroeluted. One hundred micrograms of either protein per ml of saline was mixed with 1 ml of Freund's incomplete adjuvant. This mixture was then injected intramuscularly and subcutaneously into rabbits. Two booster doses were administered at 2 week intervals, and antiserum was collected after 6 weeks. The preparation of sera against CbpA, pneumococcal surface antigen A (PsaA), and Ply was essentially as described previously (Supra, Ogunniyi, A. D., et al., 2000).

iii) Protein-labeling and Gel Electrophoresis.

For protein labeling experiments, cells were grown in CAT medium to $A_{550nm}$=0.2 and then divided into 2 ml aliquots.

The cells were then harvested, resuspended in fresh pre-warmed low-methionine labeling medium and equilibrated for 10 min at 30° C. To this was added 10 μCi of [$^{35}$S]-methionine (1000 Ci/mmol, Amersham) and the culture was then transferred to 42° C. for heat shock. The cells were harvested, resuspended in 20 μl of lysis buffer (5 mM Tris [pH 8.0], 30 mM ethylenediamine tetraacetic acid [EDTA], 0.1% Triton X-100, 0.025% [w/v] phenylmethanesulfonyl fluoride [PMSF], 1 mM dithiothreitol), and then lysed completely by sonication (on ice) as described previously (Supra, Choi et al., 1999). SDS-PAGE (either 10 or 15% polyacrylamide gel) was carried out as previously described (Laemmli, et al., 1970. Cleavage of structural proteins during the assembly of the head of bacteriophage T4. Nature 227:680-685), and the proteins were visualized with Coomassie brilliant blue staining Polyacrylamide gels were exposed to a radiation sensitive imaging plate for several days to obtain the images. The radiographic imaging data were quantitated using an image analysis system (Fujix Bio-imaging Analyzer BAS2500, Fuji Photo Film Co.).

iv) Immunoblotting.

Proteins separated by 10% SDS-PAGE were electroblotted onto polyvinylidene difluoride (PVDF) membrane and then reacted with either 1:100 dilutions of a rabbit antisera raised against heat shock proteins of *S. pneumoniae* or 1:5000 dilutions of mouse antisera raised against virulence proteins of *S. pneumoniae* (CbpA, PsaA, and Ply) as the primary antibodies. The secondary antibody was a 1:2,000 dilution of goat anti-rabbit or goat anti-mouse IgG conjugated to either horseradish peroxidase (Sigma) or alkaline phosphatase (Bio-Rad).

v) Reverse Transcription (RT)-PCR.

Total RNA was extracted using the hot acid phenol method, as described previously (Ogunniyi, A. D. et al., 2002. The genes encoding virulence-associated proteins and the capsule of *Streptococcus pneumoniae* are upregulated and differentially expressed in vivo. Microbiol. 148:2045-2053). Levels of mRNA for ply, psaA, cbpA and cps2A were quantitated by one-step real-time reverse transcription (RT-PCR) using the Promega Access RT-PCR System (Promega Biotech, Cat.# A1250). The specific primers used for the various RT-PCR assays have been described elsewhere (Supra, Ogunniyi, et al., 2002) and used at a final concentration of 50 nM per reaction. As an internal control, primers specific for the 16S rRNA (forward, 5'-GGT GAG TAA CGC GTA GGT AA-3': SEQ ID NO. 3; reverse, 5'-ACG ATC CGA AAA CCT TCT TC: SEQ ID NO. 4, Bioneer Co.) were employed. Separate RT-PCR reactions (differing only in the constituent primers) were set up (on ice) from a master mix to which Sybr®Green (Molecular Probes) had been added to a final concentration of 1:50,000. The mix was then aliquoted into tubes containing the respective upstream and downstream primers on ice and thoroughly mixed by gentle vortexing. Each mix was finally aliquoted into 0.1 ml reaction tubes and placed in a Rotor-Gene 2000 Real-Time Cycler (Corbett Research, Australia). The RT-PCR cycling conditions comprised 1 cycle at 48° C. for 39 min (for first strand cDNA synthesis), 1 cycle at 94° C. for 2 min (for AMV reverse transcriptase inactivation and RNA/cDNA/primer denaturation), followed by 40 cycles of PCR amplification comprising denaturation (94° C. for 30 secs), primer annealing (60° C. for 30 secs), and extension (72° C. for 39 secs). Amplification data were acquired at the extension step and analyzed with the Corbett Research Software Version 4.4 using the comparative critical threshold ($\Delta\Delta C_T$) values. Between RNA extracts, levels of target transcripts were normalized with reference to transcript levels obtained for the internal 16S rRNA control. All experiments were carried out in quadruplicate.

vi) Construction of clpL and clpP Deletion Mutants.

To create an insertion-deletion mutation of clpL (ΔclpL::ermB) in *S. pneumoniae*, an 860-bp ermB cassette (Obtained from Dr. Claverys, CNRS, Toulouse, France, Vasseghi, H., and J. P. Claverys. 1983. Amplification of a chimeric plasmid carrying an erythromycin-resistance determinant introduced into the genome of *Streptococcus pneumoniae*. Gene 21:285-292) was amplified with prs3 (5'-CCG GGC CCA AAA TTT GTT TGA T-3': SEQ ID NO. 5) and prs4 (5'-AGT CGG CAG CGA CTC ATA GAA T-3': SEQ ID NO. 6) from erythromycin resistant *E. coli* chromosomal DNA and used to disrupt clpL. A 410-bp fragment (clpL-up) containing part of both clpL and the 5' end of ermB was amplified with hlp3 (5'-CGG TAO CAT GAA CAA TAA TTT TAA C-3': SEQ ID NO. 7) and hlp1 (5'-ATC AAA CAA ATT TTG GGC CCG GTC AGA TGT TTC TTG AAT TTC C-3': SEQ ID NO. 8) from CP1200 DNA. A 300-bp fragment (clpL-down) containing part of both the downstream clpL sequence and the 3' terminus of ermB was amplified with hlp2 (540 -ATT CTA TGA GTC GCT GCC GAO TGT TCT AGA TGA TGG TCG TTT G-3': SEQ ID NO. 9) and hlp4 (5'-GGC CGA GCT CTT AGA CTT TCT CAC GAA TAA C-3': SEQ ID NO. 10) from CP1200 DNA. The three PCR products were used as a mixed template for PCR with hlp3 and hlp4 to produce a 1.6-kb fragment with a 1301-bp deletion of clpL (Genebank AE008411, base sequences 6374-7674) that was replaced by the ermB gene. The tripartite 1.6-kb fragment was subsequently introduced into either *S. pneumoniae* CP1200 or D39strains by transformation, and recipient bacteria that had integrated the recombinant fragment into the chromosome by homologous recombination were selected by resistance to erythromycin. Transformants were screened for the correct deletion by PCR and immunoblot analysis (not shown). CP1200 and D39 clpL$^-$mutants, HYK1 and HYK304, respectively, contained the correct deletion within clpL and were used for further studies. ClpP$^-$mutants in either CP1200 (HYK2) or D39 (HYK302), with a deletion of 95-bp (Genebank AE008443, base sequences 5621-5715), were constructed using the same strategy except for the primers (see, e.g., appended SEQ ID NO. 2, showing only base sequences 5416 to 6006 of section 59 of 184 of the complete genome of *S. pneumoniae*; accordingly, base sequences 206 to 300 of SEQ ID NO. 2 correspond and to said base sequences 5621-5715 of section 59 of 184 of the complete genome of *S. pneumoniae*); for clpP up (234-bp), hpp3 [5'-: CGA ATT CAT GAT TCC TGT AGT TAT-3': SEQ ID NO. 11] and hpp11 [5'-ATT CTA TGA GTC GCT GCC GAC TCA GAA CCA CCT GGT GTA TTG A-3': SEQ ID NO. 12] and for clpP-down (319-bp), hpp10 [5'-ATC AAA CAA ATT TTG GGC CCG GAT CGC ATC AAG TGG AGC AAA A-3': SEQ NO. 13] and hpp6 [5'- CGA GCT CTT AGT TCA ATG AAT TGT TG-3': SEQ ID NO. 14].

vii) Over-expression of ClpL in *E. coli*.

Figure 2:
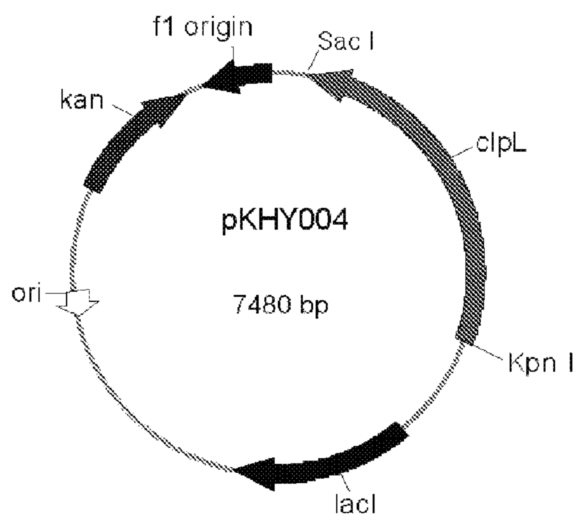
FIG. 2 shows a structure of pKHY004 expression vector.

To overexpress His$_6$-tagged ClpL in *E. coli*, the clpL ORF was amplified with hlp3 and hlp4 from CP1200 DNA. The fragment was digested with KpnI and SacI and cloned into the KpnI and SacI sites of pET30(a) (Novagen) to generate plasmid pKHY004 (FIG. 2). His$_6$-tagged protein was expressed in *E. coli* and subjected to DEAE-Sepharose fast Flow™ chromatography (Amersham Pharmacia) eluted with a 0.1 to 0.4 M NaCl gradient. The fractions containing ClpL were pooled and purified on a nickel-nitriloacetic acid column according to the manufacturer's instructions (Novagen) with minor modifications. Bound His$_6$-tagged protein was washed with 40 mM imidazole buffer, eluted with 0.4 M imidazole buffer (pH 7.9), and dialyzed against 20 mM Tris-HCl (pH 7.8), 5 mM $MgCl_2$. The protein was >95% pure as judged by SDS-PAGE and staining with Coomassie brilliant blue 8250 (data not shown).

viii) Determination of Chaperone Activity.

Chaperone activity of ClpL was determined as described previously (Kudlicki, W. et al, 1997. Renaturation of rhodanese by translational elongation factor (EF) Tu. Protein refolding by EF-Tu flexing. J. Biol. Chem. 272:32206-32210) with a modification as follows. Rhodanese (Sigma, USA) (9 μM) was denatured in 200 mM potassium phosphate buffer (pH 7.6) containing 1 mM β-mercaptoethanol and 8 M urea for 1 hour at 25° C. Spontaneous and ClpL-assisted refolding was initiated by diluting 2.5 μl of denatured enzyme in 8 M urea to a final volume of 250 μl of a solution containing 50 mM Tris-HCl (pH 7.8), 200 mM β-mercaptoethanol, 5 mM sodium thiosulfate, 10 mM $MgCl_2$, 10 mM KCl. The final concentration of rhodanese in the refolding reaction was 90 nM. The refolding reaction was carried out for 30 min at 25° C. Chaperone activity of ClpL was measured by refolding of rhodanese into its native conformation. Enzyme activity of rhodanese was determined as previously described (Sorbo, B. H. et al., 1953. Crystalline rhodanese. I. Purification and physicochemical examination. Acta Chem. Scand. 7:1129-1136).

ix) Virulence Studies.

Intraperitoneal (i.p.) challenge with a highly virulent capsular type 2 strain (D39) and its isogenic clpP- and clpL-mutants (HYK302 and HYK304, respectively) was performed to evaluate the effect of mutating clpL or clpP on the virulence of *S. pneumoniae*. Bacteria were cultured at 37° C. overnight on brain heart infusion agar (Difco Laboratories, USA) containing 10% [vol/vol] horse serum, or on Todd Hewitt agar (Difco Laboratories, USA) (supplemented with erythromycin as required) and then grown in serum broth {brain heart infusion agar (Difco Laboratories, USA) containing 10% [vol/vol] horse serum, or Todd Hewitt broth (Difco Laboratories, USA)} for 3 h at 37° C. to give ca. $10^8$ CFU/ml (Supra, Ogunniyi, A. D. et al., 2000). Each bacterial culture was then diluted in serum broth to ca. $10^6$ CFU/ml, and groups of 10 BALB/c mice were infected i.p. with 0.1 ml volumes of either D39, HYK302 or HYK304. The survival of the challenged mice was monitored four times daily for the first 5 days, twice daily for the following 5 days, and daily until 21 days post-challenge.

x) Pneumolysin Assay.

Hemolytic activity was determined as previously described (Supra, Hanahan, D., 1983) with a minor modification. The pneumococci (D39, HYK302, HYK304) grown in THY broth to early-mid log phase (absorbance at 600 nm=0.05-0.1) were harvested by centrifugation at 3900×g for 10 min at 4° C. and resuspended in phosphate buffered saline. Sodium deoxycholate was added to a final concentration of 0.1% and then incubated at 37° C. for 10 min. After centrifugation of the samples, the supernatant was withdrawn and serially diluted. Hemolytic activity was determined by incubation with an equal volume of 1.5% washed human red blood cells in 96 well microtiter plates. Hemolytic titer was determined as the reciprocal of the estimated dilution at which 50% of erythrocytes were lysed at 540 nm.

xi) Statistics.

Statistical analysis was performed using a paired or unpaired Student's t test. Data presented are mean±standard deviation of the mean for 2 to 4 independent experiments. Differences in median survival times between groups were analyzed by the Mann-Whitney U test (two-tailed) and differences in overall survival rate between groups were analyzed by the Fisher Exact test.

2. Results i) Characterization of ClpL.

Figure 3:
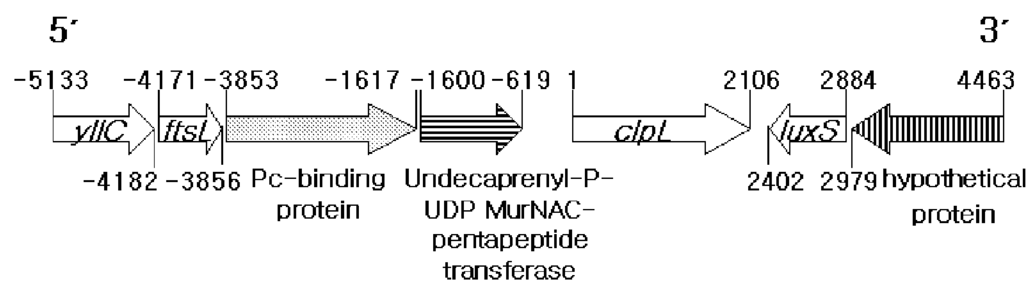
FIG. 3 shows a map indicating relative site of *S. pneumoniae* clpL locus.

Previously, an 84-kDa HSP was identified as CIpL by N-terminal amino acid sequencing (Supra, Choi et al., 1999). Members of the Clp family contain two highly conserved ATP-Binding regions (ATP-1 and ATP-2), each of which contains a consensus sequence for adenine nucleotide binding (Gottesman, S. et al., 1990. Conservation of the regulatory subunit for the Clp ATP-dependent protease in prokaryotes and eukaryotes. Proc. Natl. Acad. Sci. U.S.A. 87:3513-3517). To confirm that putative ClpL of *S. pneumoniae* is indeed a member of the Clp family, oligonucleotides from the N-terminal amino acid sequence (5'-GAT GAA YAA YAA YTT YAA YAA YTT YAA-3': SEQ ID NO. 15) and the second ATP-binding site for Clp members (5'-GTY TTN CCN CAN CCN GYN GG-3', where Y=T or C, N=A, C, G or T: SEQ ID NO. 16), which was the most conserved amino acid sequence (PTGVGKT) of the clp family, were used for PCR amplification of CP1200 chromosomal DNA. PCR yielded a 1.37-kb DNA fragment expected from the size of *L. lactis* ClpL. This was cloned into pGEM-T (Promega) to generate plasmid pG8413. Sequence analysis of the cloned fragment demonstrated homology to *L. lactis* clpL and bovine clp genes (data not shown). The complete clpL gene was then identified in the TIGR *S. pneumoniae*type 4 genome using BLAST analysis. Moreover, the clpL homologue in *S. pneumoniae* R6 showed 98% identity with that of type 4 clpL homologue, and CP1200 clpL revealed high sequence homology with that of R6 clpL (data not shown). The organization of this region of the genome is shown in FIG. 3.

A detailed analysis of the sequence of clpL showed an ORF of 2103-bp encoding a putative polypeptide of 701 amino acids with a molecular weight of 77,699 daltons and a pI (isoelectric point) of 4.99. Analysis of the nucleotide sequence showed that *S. pneumoniae* clpL has a sigma A type promoter (TTGACC-17-bp-TATATT) 240-bp upstream of the ATG codon. In the upstream of clpL there is CtsR repressor binding sequence GTC AAA NAN RGT CAA A (R=A or G) (SEQ ID NO. 17), which has been found adjacent to clp genes in several organisms. Thus, clpL may be regulated by CtsR. A gene 619-bp upstream from clpL, encodes a putative undecaprenyl-p-UDP-MurNAC-pentapeptide transferase and is in the same orientation. The gene downstream of clpL, encoding LuxS, is in the opposite orientation (FIG. 3), suggesting that clpL is organized as a monocistronic transcription unit.

BLAST analysis indicated that pneumococcal ClpL has high homology to all members of the Clp family in the two conserved ATP-binding regions (p-loops) at amino acids 121-128 (GDAGVGKT) and 391-398 (GSTGVGKT). Eight amino acids (MDDLFNQL) at positions 11 to 18 in the hydrophilic N-terminal region were also absolutely conserved with the bovine Clp-like protein and *L. lactis* ClpL. The pneumococcal ClpL ATPase shows strongest homology with a bovine Clp-like protein (76% identity and 88% similarity) and *L. lactis* ClpL (59% identity and 76% similarity). It also shows high homology to that of other species (data not shown).

ii) Transient Induction but High Stability of ClpL after Heat Shock.

Figure 4A:
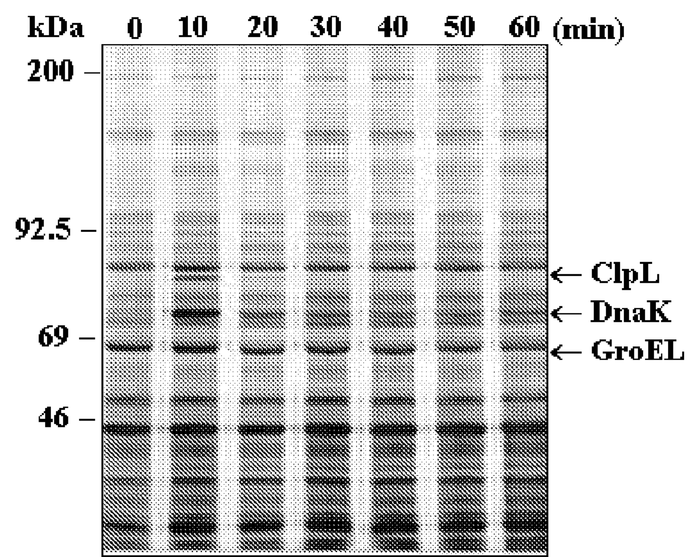
FIGS. 4*a* to 4*c* show an experiment result of transient induction and stability of *S. pneumoniae* ClpL after heat shock.

Major HSPs, ClpL, DnaK, and GroEL, which have molecular weights of 84-, 73-, and 65-kDa, respectively, have been identified by N-terminal amino acid sequencing of corresponding *S. pneumoniae* proteins after heat shock. The coordinate or independent control of HSP expression has not been determined, hence we examined the kinetics of HSP synthesis by pulse-labeling with [$^{35}$S]-methionine. Cells grown at 30° C. to mid-exponential phase were heat shocked by shifting the temperature to 42° C., and then pulse-labeled for 10 min with [$^{35}$S]-methionine. Two ml of the culture were harvested, and the cells were lysed in lysis buffer by sonication. The cell lysates were then analyzed by SDS-PAGE, and the protein bands were visualized by autoradiography. The result revealed that the induction of HSPs peaked at 10 min after the upshift in temperature and then rapidly diminished to baseline levels (FIG. 4*a*). After incubating the cells at 42° C. for 10 min, synthesis of ClpL, DnaK, and GroEL, was increased 11.3±0.8, 5.0±0.3, and 2.7±0.2 fold, respectively, relative to the control. Although the GroEL band was very close to the nearby protein band, a higher magnification of the autoradiogram clearly showed that GroEL was induced (see FIG. 4*b*).

Figure 4B:
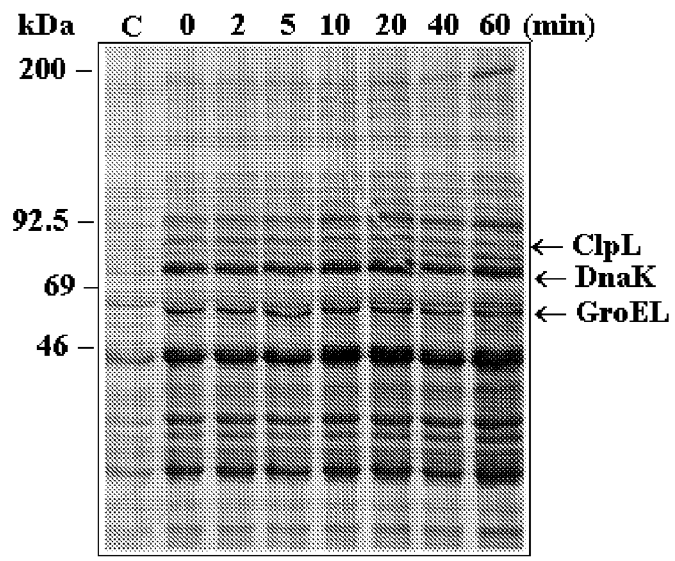
Figure 4C:
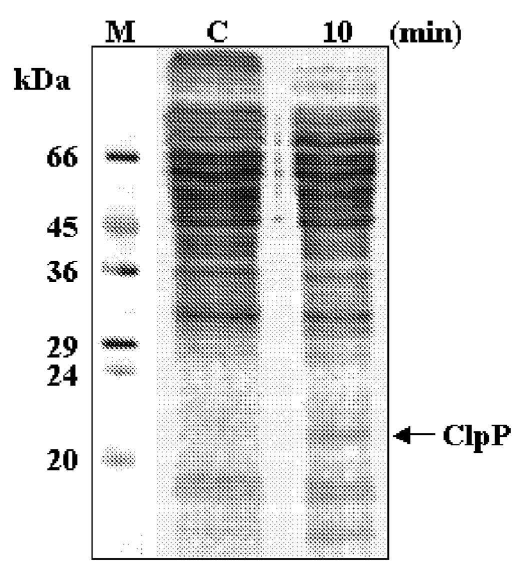

In addition, in order to determine the stabilities of heat shock proteins, CP1200 cells grown at 30° C. to mid-exponential phase ($A_{550}$=0.2) were heat stressed at 42° C. for 10 min and pulse-labeled with [$^{35}$S]-methionine at that time, and then the cell cultures were returned to 30° C. followed by chasing with excess nonradioactive methionine for the indicated times. Two ml of cultures were harvested, and the cells were lysed by sonication. The cell lysates were then analyzed by SDS-PAGE, and protein bands were visualized by autoradiography (FIG. 4*b*). Synthesis of the major HSPs after the initial 10 min exposure at 42° C. rapidly leveled off to 2.0±0.2, 2.2±0.3, and 1.2±0.1-fold, respectively, relative to the non-heat-shocked control, suggesting that synthesis of HSPs reached a new steady state level. Similar to the results presented in FIG. 4*a*, pulse-labeling for 2.5 min with [$^{35}$S]-methionine from 0 to 15 min showed that GroEL, DnaK, and ClpL were made early, and the induction of HSPs peaked at around 5 min after temperature upshift, but fell off to the steady state after 7.5 min and resulted in net 1.5 to 2 fold increases relative to the control (data not shown). These results indicate that these HSPs, although in different classes, have the same kinetics of induction. Also, the increase in the rate of synthesis upon heat shock is similar to the increase in mRNA level of clpL and groEL, respectively, in the stationary growth phase of the pneumococcus (Saizieu, A. et al., 1998. Bacterial transcript imaging by hybridization of total RNA to olignucleotide arrays. Nature Biotechnol. 16:45-48). Since the ATPase subunit of Clp members forms a complex with the ClpP serine protease, CP1200 cells grown at 30° C. to mid-exponential phase ($A_{550}$=0.2) were heat shocked for 10 min at 42° C., were pulse-labeled with [$^{35}$S]-methionine, and then the cell cultures were returned to 30° C. followed by chasing with excess nonradioactive methionine for the indicated times. Two ml of cultures were harvested, and the cells were lysed by sonication. The resulting proteins were then analyzed by SDS-PAGE, and protein bands were visualized by autoradiography (FIG. 4*c*). The result revealed induction of a 21-kDa HSP after heat shock, which was identified as ClpP by N-terminal amino acid sequencing. In FIG. 4*c*, Lane C is not stressed. Numbers on top in FIGS. 4*a* to 4*c* show lapsed time (min) after return to the non-stress condition. The heavy arrows indicate major HSPs. Molecular sizes in kDa are indicated on the left.

Figure 5A:
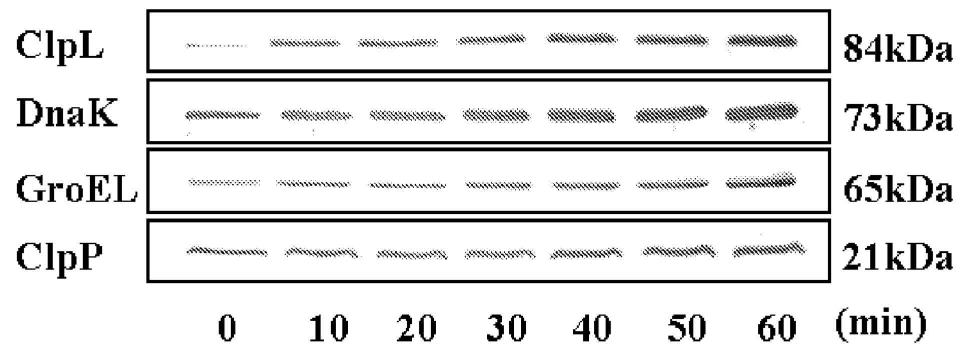
FIGS. 5*a* to 5*b* represent steady accumulation of ClpL after heat shock.
Figure 5B:
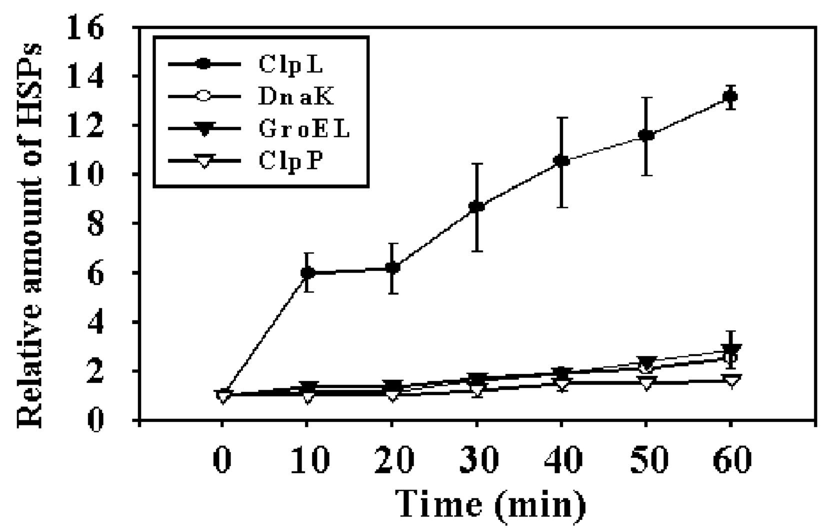

HSPs are immunogenic in some pathogens (Kaufmann, S. H. E. et al., 1994. Heat shock proteins as antigens in immunity against infection and self, p. 495-532. In R. I. Morimoto, A. Tissieres, and C. Georgopoulos (ed.), Biology of Heat Shock Proteins and Molecular Chaperones. Cold Spring Harbor, N.Y.: Cold Spring Harbor Laboratory Press), and persistence of HSPs may help in the survival of the pathogens in the host. Therefore, the stability of HSPs was examined. Bacteria were heat-shocked at 42° C. for 10 min, pulse-labeled at that time, returned to 30° C., and then chased with non-radioactive methionine for various lengths of time. When we examined for HSPs after 1 to 60 min, there was no detectable decrease in the amount of radioactive ClpL, DnaK, or GroEL, i.e., the HSPs produced during heat shock persisted through the temperature downshift for 60 min (FIG. 5*b*). Interestingly, immunoblot analysis using HSPs of *S. pneumoniae* revealed that the absolute amount of the ClpL increased significantly and steadily (up to 14 fold by 60 min) during the sustained heat shock. FIGS. 5*a* and 5*b* show that ClpL increased seadily after heat shock. Whole cell lysates which were obtained from exponentially grown *S. pneumoniae* cells exposed to 42° C., were subjected to immunoblot analysis. *S. pneumoniae* cells grown at 30° C. until $A_{550}$=0.3 were heat shocked at 42° C. for the indicated times, and then the culture was harvested and resuspended in lysis buffer. The cells were lysed by sonication, and then ten μg of proteins were separated by SDS-PAGE and reacted with antisera to ClpL, DnaK and GroEL. In case of ClpP, 30 μg of proteins were used for SDS-PAGE followed by immunoblot analysis (FIG. 5*a*). Densitometric analysis of relative levels of ClpL, ClpP, DnaK and GroEL after heat shock is shown in FIG. 5*a*. Figure shows the standard deviation from two independent experiments (FIG. 5*b*). The amount of DnaK and GroEL was increased by 2.4 and 3.4 fold, respectively, during a 60 min period (FIGS. 5*a* and 5*b*), but thereafter there was a reduction in the amounts of all the HSPs (data not shown). These results indicate that ClpL is fairly stable in *S. pneumoniae.* iii) Phenotype of clpL$^-$ and clpP$^-$ Mutants.

Figure 6A:
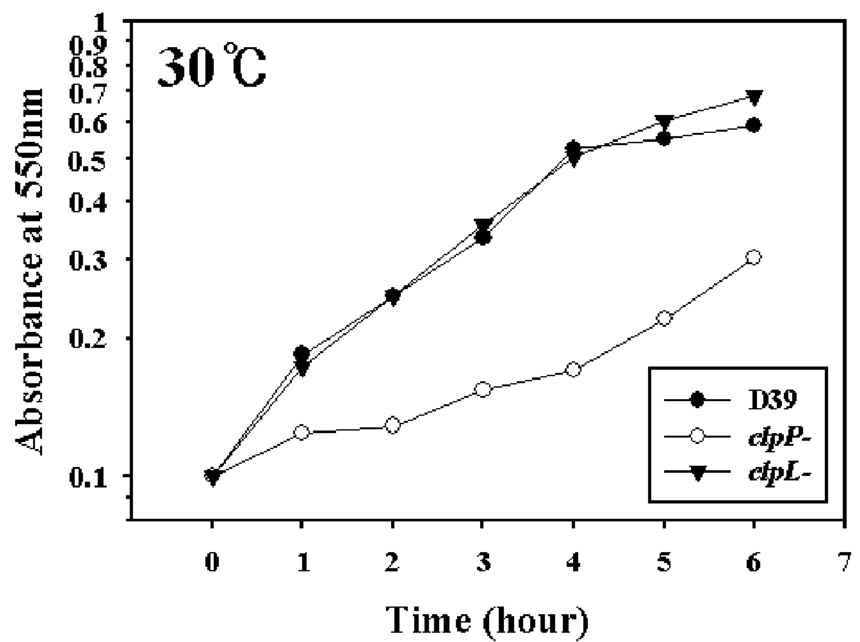
FIGS. 6*a* to 6*c* show growth of D39 and its clpL$^-$ and clpP$^-$ mutants.
Figure 6B:
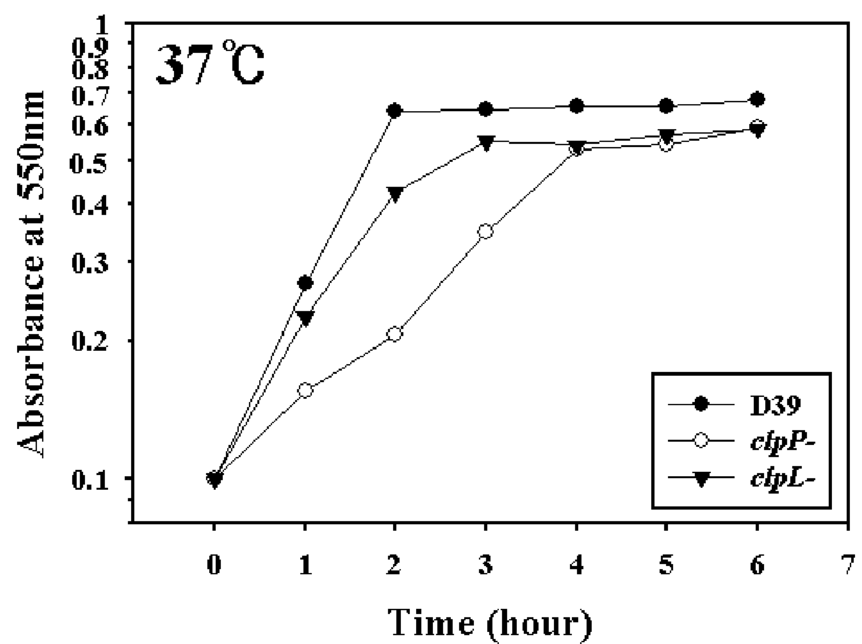
Figure 6C:
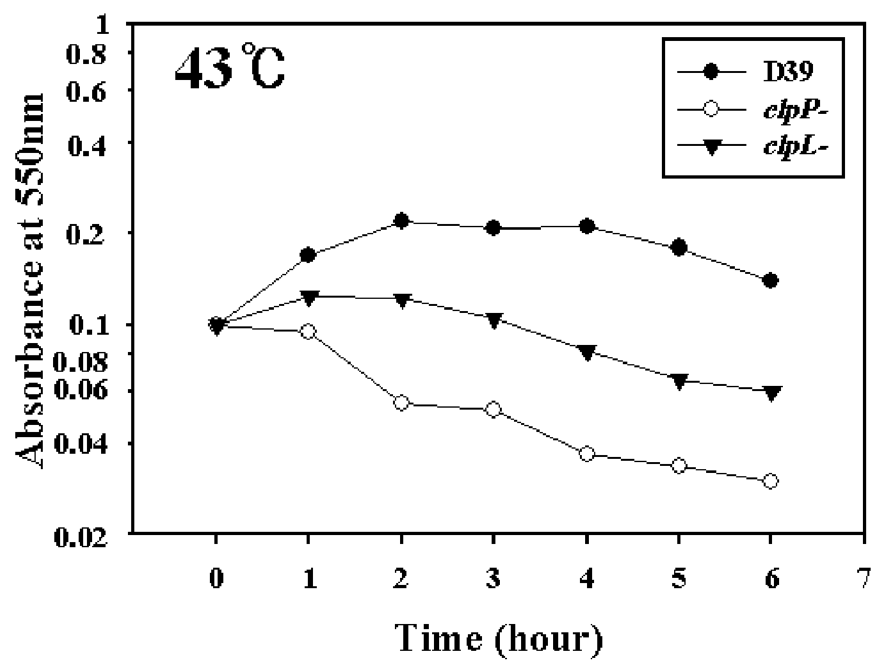

To construct clpL$^-$ and clpP$^-$ mutants, a DNA fragment containing either ΔclpL::ermB or ΔclpP::ermB insertion was amplified by PCR and incorporated into the chromosome by transformation as described in Materials and Methods. The insertion mutation was confirmed by PCR and by immunoblot analysis to demonstrate the absence of ClpL or ClpP, respectively. Cultures of D39 and its isogenic clpL$^-$ (HYK304) and clpP$^-$ (HYK302) mutants were grown to an absorbance of 0.1 at 550 nm. The temperature was then shifted from 37° C. to 43° C. and the cultures were incubated at the indicated times. The results were shown in FIG. 6. The growth rate of the D39 derivative HYK304 carrying ΔclpL::ermB was similar to that of the parent at 30° C., but grew slower at 37° C. with a doubling time of 55 min, compared to about 40 min for the parent (FIGS. 6*a* to 6*c*). Thus, ClpL does not seem to be essential for the growth of *S. pneumoniae* at 30° C. and 37° C. In contrast, HYK302 carrying the ΔclpP::ermB mutation showed severely impaired growth at both 30° C. (doubling time=270 min) and 37° C. (doubling time=100 min) compared to the parent strain (100 and 40 min, respectively). At 43° C., the growth of D39 increased for the first 2 hr period, but decreased thereafter. The viability of the parent strain was maintained over a 45 min period at 42° C.; however, beyond 45 min, the viability started to drop (data not shown). At 43° C., the growth of clpL$^-$ and clpP$^-$ mutants (HYK304 and HYK302, respectively) was impaired. Furthermore, isogenic CP1200 derivatives HYK1 and HYK2 showed similar growth patterns as those of HYK304 and HYK302, respectively (data not shown).

iv) Induction of ClpL in clpP$^-$ Mutation.

Figure 7A:
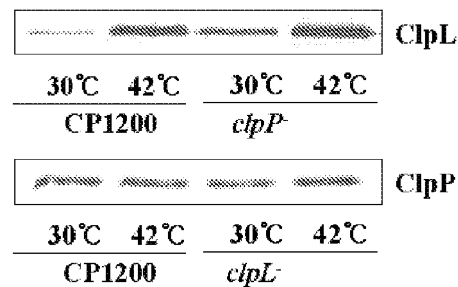
FIGS. 7*a* to 7*b* show induction of ClpL in clpP$^-$ mutant of *S. pneumoniae* CP1200.
Figure 7B:
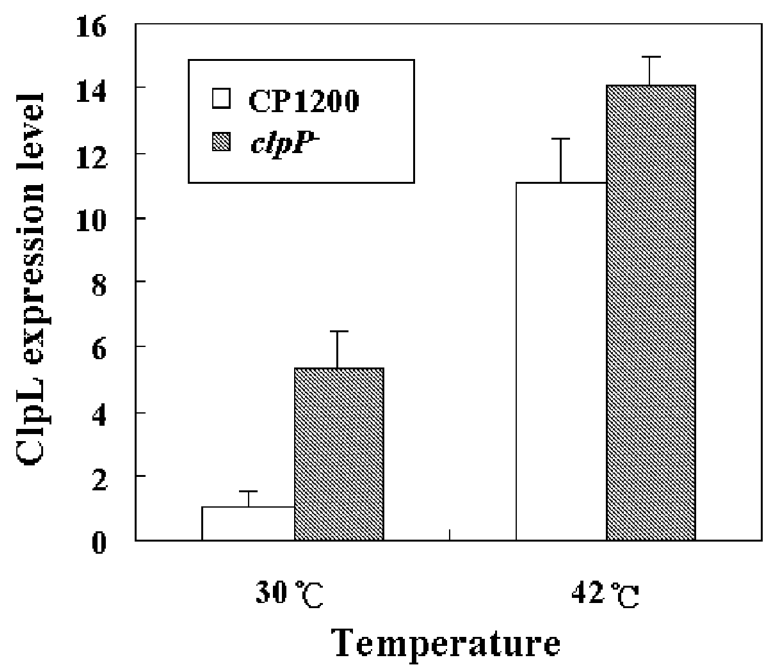

From the results of the previous studies that ClpL and ClpP seem to be regulated by the same CtsR, and that ClpP is involved in CtsR degradation, it is likely that ClpL might be controlled by ClpP. To examine this possibility, we determined the amount of ClpL and ClpP using either CP1200 or its clpL or clpP negative mutants. Exponentially grown *S. pneumoniae* CP1200 ($A_{550}$=0.3) and its isogenic clpL⁻ and clpP⁻ derivatives were heat-shocked at 42° C. for 30 min. Proteins from 3 ml of culture were subjected to immunoblot analysis using either anti-ClpL or ClpP polyclonal sera. In wild type (CP1200) and the clpL⁻ mutant (HYK1), ClpP was detected at 30° C., but after the cells were heat shocked for 30 min, the amount of ClpP was marginally increased as shown in FIGS. 7*a* and 7*b*. Although ClpL was induced, the amount of ClpL in the uninduced culture was greater in a clpP⁻ mutant (HYK2) than in the wild type, suggesting that ClpP represses expression of ClpL (FIGS. 7*a* and 7*b*).

v) Chaperone Function of ClpL.

Since HSPs promote secretion and assist in the proper folding and translocation of proteins (Craig, E. A. et al., 1993. Heat shock proteins: Molecular chaperones of protein biogenesis. Microbiol. Rev. 57:402-414), chaperone activity of ClpL in *S. pneumoniae* was examined. To measure chaperone activity quantitatively, refolding of a denatured protein into its native conformation is used (Mendoza, J. A. et al., 1991. Unassisted refolding of urea unfolded rhodanese. J. Biol. Chem. 266:13587-1359132). Since unassisted refolding of rhodanese occurs relatively slowly (Supra, Mendoza, J. A. et al.) and rhodanese activity can be determined by a simple and sensitive assay, refolding of denatured rhodanese has been used extensively to study protein folding. Histidine-tagged ClpL (pKHY004) (FIG. 2) was overexpressed in *E. coli*, purified, and used for determination of refolding activity. Under the test conditions, denatured rhodanese showed only 2.8~7.7% of the native rhodanese activity as shown previously (Supra, Craig, E. A. et al.), indicating that spontaneous refolding of denatured rhodanese occurs inefficiently when diluted 100-fold from an 8 M urea solution. This activity is expressed as a percentage of the activity of native rhodanese carried through the same procedure. Inclusion of ClpL in the refolding reaction mixture in an approximately 3 molar excess amount to denatured rhodanese increased renaturation to almost 10% of the native rhodanese activity. However, when a 12-fold excess of ClpL was added to denatured rhodanese, it increased activity to 30% of the native level. Increasing the amount of ClpL added above this concentration yielded a little further renaturation in the presence of ATP (Table 2). These results demonstrated that ClpL could function independently as a chaperone to refold the denatured protein as shown previously for ClpA in *E. coli*.

TABLE 2

ClpL-dependent in vitro refolding of denatured rhodanese.

| ClpL Concentration | Rhodanese activity (%) |
|---|---|
| — | 4.3 ± 1.8 |
| ClpL 90 Nm | 9.0 ± 4.2* |
| ClpL 270 nM | 9.5 ± 3.2** |
| ClpL 541 nM | 15.2 ± 7.2** |
| ClpL 1.08M | 30.1 ± 14.0** |
| ClpL 1.6M | 35.7 ± 14.0** |
| ClpL 2.2M | 35.9 ± 6.5** |

*Significantly different from control (no ClpL), P < 0.05.

**Significantly different from control, P < 0.001.

Denatured rhodanese (90 nM final concentration) was incubated at 37° C. for 1 hr alone or together with ClpL in the presence of 2 mM ATP. The activity of the refolded enzyme was measured after 60 min incubation at 25° C. and is expressed as percentage of the activity of the same amount of native enzyme incubated at 25° C. under the same conditions. The mean value and standard deviation of 5 independent experiments are shown.

vi) Modulation of Expression of Virulence Associated Factors by Heat Shock.

Figure 8:
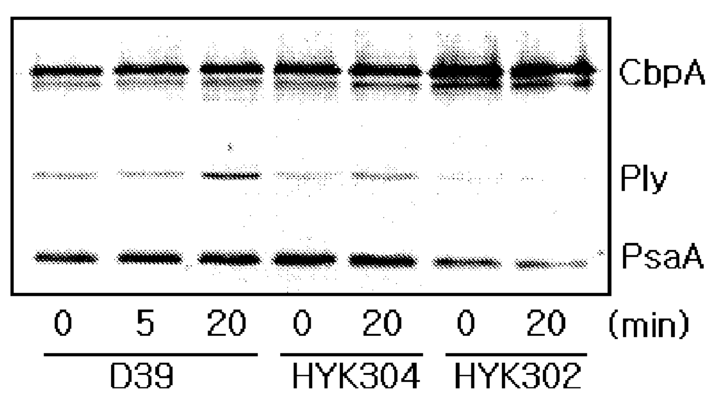
FIG. 8 shows induction of virulence associated genes by heat shock.

Environmental stress including heat shock and starvation can affect expression of virulence factors (Mekalanos, J. J. 1992. Environmental signals controlling expression of virulence genes determinants in bacteria. J. Bacteriol. 174:1-7). Hence, the effect of heat shock on expression of virulence associated factors in the encapsulated strain D39, and its clpP⁻ (HYK302) and clpL⁻ (HYK304) mutants, was determined by immunoblot analysis using antibodies against choline-binding protein A (CbpA), PsaA, pneumococcal surface protein A (PspA), Ply, and autolysin (LytA). Exponentially grown encapsulated *S. pneumoniae* D39 ($A_{600}$=0.1) and its isogenic clpP⁻ (HYK302) and clpL⁻ (HYK304) derivatives were heat-shocked at 42° C. for 20 min. 0.6 ml of culture was centrifuged, and the cell pellets were resuspended in lysis buffer followed by boiling for 3 min. Subsequently, cell lysates were subjected to immunoblot analysis using a mixture of polyclonal antisera raised against CbpA, Ply, and PsaA. The relative positions of CbpA, Ply and PsaA are indicated in FIG. 8. Unexpectedly, Ply was induced after heat shock in the wild type D39 as well as in the clpL⁻ mutant. PsaA was also induced slightly in D39 after heat shock, but it was not induced in the clpL⁻ mutant. In contrast, in the clpP⁻ mutant, CbpA was induced but expression of Ply and PsaA was decreased (FIG. 8). PspA and LytA levels did not change after heat shock regardless of genetic background (result not shown). To confirm the increase of Ply expression after heat shock, hemolytic activity of the Ply in cell lysates was determined. Although Ply activity was increased 1.8 fold in D39 after heat shock, it was not increased in the clpP⁻ mutant (Table 3).

TABLE 3

Effect of heat shock on hemolytic activity of pneumolysin[a].

| Strains | Hemolytic unit 30° C. | Hemolytic unit 42° C. | % increase after heat shock |
|---|---|---|---|
| D39 | 9,331 ± 2,347 | 16,515 ± 4,592 | 177* |
| HYK304 (clpL⁻ mutant) | 10,210 ± 1,429 | 13,477 ± 3,155 | 132 |
| HYK302 (clpP⁻ mutant) | 13,063 ± 2,859 | 15,414 ± 2,489 | 118 |

([a]Mean ± standard deviation of three independent experiments. *: P < 0.05)

Hemolytic activity in cultures is equivalent to $A_{600}$=1. Fifty μl of cell lysate was serially diluted (1:1) into 50 μl of phosphate-buffered saline. Then 50 μl of a 1.5% suspension of human red blood cells was added to each well. The plate was then incubated for 30 min at 37° C. The hemolytic units were calculated from the well at which 50% hemolysis had occurred. These results demonstrated that heat shock increased Ply expression in the wild type and the clpL⁻ mutant, possibly contributing to a potential gain in virulence upon stress challenge, but this did not occur in the clpP⁻ mutant.

Figure 9:
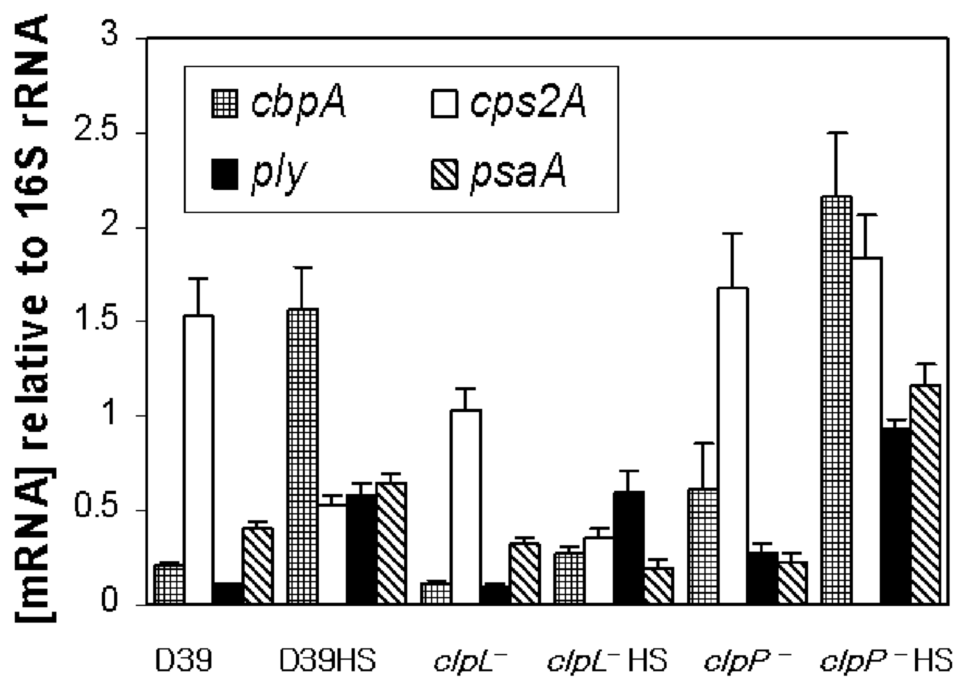
FIG. 9 shows relative mRNA concentrations of cbpA, cps2A, ply and psaA, in D39, clpL$^-$ and clpP$^-$ mutants before and after heat shock as determined by real-time RT-PCR.

In *Yersinia enterocolitica*, the ClpP protease repressed the expression of both ail transcript level and cell surface-expressed Ail protein (Pederson, K. J., S. Carlson, and D. E. Pierson. 1997. The ClpP protein, a subunit of the Clp protease, modulates ail gene expression in *Yersinia enterocolitica*. Mol. Microbiol. 26:99-107). This prompted us to examine the modulation of virulence gene expression at the mRNA level in *S. pneumoniae*. RNA was prepared from cultures and mRNA levels of ply, cbpA, psaA and the capsule synthesis gene cps2A were determined by RT-PCR. The results were shown in FIG. 9. In FIG. 9, between RNA extracts, levels of individual mRNA species were corrected with reference to that obtained for the internal 16S rRNA control. Data points represent means±standard deviations of quadruplicate samples from each RNA extract. At 30° C., expression of cbpA in the clpL⁻ mutant was decreased relative to that of D39 (P=0.001) but increased in the clpP⁻ mutant (P=0.01). Although no significant changes in expression of ply and psaA in the wild type and clpL⁻ mutant were detected, in the clpP⁻ mutant, expression of ply was increased 2.5 fold (P<0.01), but expression of psaA was decreased by half (P<0.01). After heat shock, cbpA mRNA levels were increased 7.48-, 2.39-, and 3.48-fold (P<0.001, P<0.001, P=0.001, respectively) relative to 30° C. levels in D39, clpL⁻, and clpP⁻ mutants, respectively. Similarly, mRNA levels of ply were increased 5.27-, 6.0-, and 3.48-fold relative to 30° C. levels in D39, clpL⁻, and clpP⁻ mutants, respectively (P<0.001 in all cases). After heat shock, expression of cps2A was significantly decreased relative to 30° C. levels in both D39 and the clpL⁻ mutant (P=0.001 in both cases). The expression of cps2A in the clpP⁻ mutant was increased after heat shock, but the increase was not statistically significant. In contrast, heat shock increased the mRNA level of psaA 1.6- and 5.04-fold in D39 and the clpP⁻ mutant, respectively (P<0.01, P=0.001, respectively), but it was decreased in the clpL⁻ mutant (P<0.01; FIG. 9). These results suggest that the clpL⁻ mutation may negatively affect the expression of psaA whereas clpP⁻ mutation may positively affect the expression of cps2A in some unknown way. These findings provide evidence that clpL and clpP as well as heat shock modulate a variety of virulence associated genes to cope with new environmental challenges.

vii) Effect of clpL and clpP Mutation on Virulence.

Figure 10:
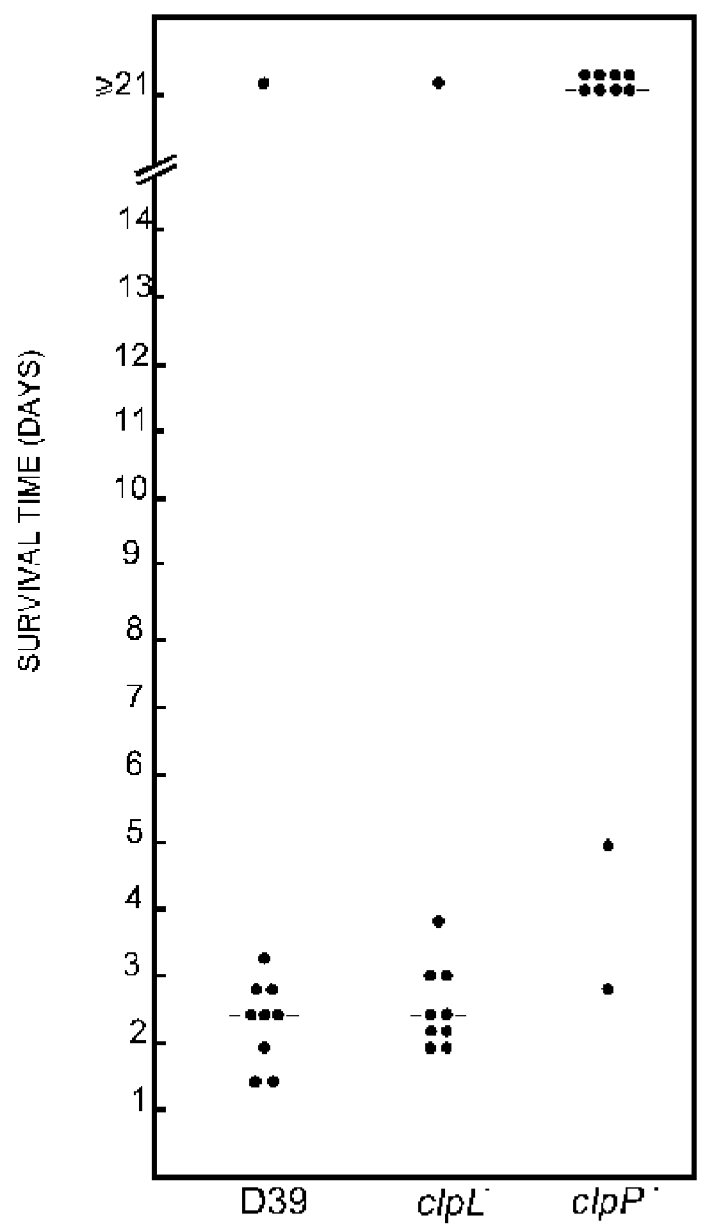
FIG. 10 shows survival times of mice after intraperitoneal challenge.

To further investigate the effect of clpL⁻ and clpP⁻ mutations on virulence of D39, the survival time of mice after i.p. infection with ca. $10^5$ CFU of pneumococci was measured. Groups of 10 BALB/c mice were infected with approximately $10^5$ CFU of D39 or its clpP⁻ (HYK302) or clpL⁻ (HYK304) derivative. The results were shown in FIG. 10. In FIG. 10, each data point represents one mouse, horizon represents median survival time for each group. The median survival time for mice in the groups infected with the parent strain (D39) and the clpL⁻ mutant was 55 hr and 60 hr, respectively. This difference was not statistically significant. However, the group of mice infected with the clpP⁻ mutant became sick 2-3 days from post-infection, but most gradually recovered 4-5 days from post-infection. Only two mice challenged with the clpP⁻ mutant died after 67 and 119 hr (FIG. 10). The differences in median survival time and overall survival between the group infected with the clpP⁻ mutant and the groups infected with either D39 or the clpL⁻ mutant were highly significant (P<<0.001 in all cases). This result indicates that ClpP function is critical for virulence factor expression in *S. pneumoniae.*

3. Discussion

In this study, we identified an ATP-dependent Clp protease AAK74513 in *S. pneumoniae* as the clpL homologue. ClpL homologues have been identified in several Gram-positive organisms (*L. lactis* X62333; *S. aureus* AP003365, AP003137; *S. pyogenes* AE006538, AE004092; *Lactobacillus rhamnosus* AF323526) but not in Gram-negative organisms, and so ClpL, like ClpE, seems to be specific to Gram-positive organisms (Derre, I. Et al., 1999. ClpE, a novel type of HSP100 ATPase, is part of the CtsR heat shock regulon of *Bacillus subtilis*. Mol. Microbiol. 32:581-593).

Using scanning densitometry of immunoblot analysis, we found that *S. pneumoniae* expressed high basal levels of DnaK, GroEL, and ClpP but not ClpL at 30° C. These levels increased up to twofold upon exposure of the organism to heat shock over a 40 min period. However, pulse-labeling of proteins for 10 min with [$^{35}$S]-methionine demonstrated rapid and transient induction of all the HSPs, indicating that DnaK, GroEL and ClpP were expressed constitutively in large amounts at 30° C. Moreover, persistence of ClpL, DnaK and GroEL upon return to 30° C. indicates that HSPs do not appear to be actively degraded upon return to normal culture conditions. Since HSPs function as chaperones and promote renaturation of unfolded proteins and are induced during infection in a wide variety of bacterial pathogens, survival in vivo could be enhanced by the stabilizing effect of HSPs on bacterial macromolecular complexes in hostile environments. Therefore, persistence of the HSPs upon return to normal conditions and induction of virulence proteins such as PsaA and Ply by heat shock might contribute or enhance virulence of the pneumococcus. The major HSP, DnaK, is highly immunogenic in *S. pneumoniae* (Hamel, J., D. Martin, and B. B. Brodeur. 1997. Heat shock response of *Streptococcus pneumoniae*: identification of immunoreactive stress proteins. Microb. Pathog. 23:11-21) and there is substantial evidence in the literature that HSPs are immuno-dominant antigens in infections by various pathogens (Supra, Kaufmann, S. H. et al., 1994). Whether the pathogenic life-style of *S. pneumoniae* necessitates high levels of DnaK and ClpL, and whether ClpL associates with the specific substrate and forms a complex with ClpP for proteolysis is the subject of an ongoing study using recombinant proteins.

It is well documented that mutation in HSP genes impacts on adherence and virulence in many pathogens. The stress-induced ClpP serine protease contributes to virulence in *Salmonella typhimurium* (Webb, C. et al., 1999. Effects of DksA and ClpP protease on sigma S production and virulence in *Salmonella typhimurium*. Mol. Microbiol. 34:112-123) and modulates adhesion invasion locus (ail) gene expression in *Yersinia enterocolitica* (Pederson, K. J. et al., 1997. The ClpP protein, a subunit of the Clp protease, modulates ail gene expression in *Yersinia enterocolitica*. Mol. Microbiol. 26:99-107). In *Listeria monocytogenes*, ClpP is essential for intracellular parasitism and virulence (Gaillot, O. et al., 2000. The ClpP serine protease is essential for the intracellular parasitism and virulence of *Listeria monocytogenes*. Mol. Microbiol. 35:1286-1294). Our results indicate that ClpP also plays an essential role in the virulence of *S. pneumoniae*, and supports the recent finding of Robertson et al. (Robertson, G. T. et al., 2002. Global transcriptional analysis of clpP mutations of type 2 *Streptococcus pneumoniae* and their effects on physiology and virulence. J. Bacteriol. 184:3508-3520).

In this study, we have demonstrated that the mRNAs for virulence associated genes such as cbpA, ply, and psaA were upregulated by heat shock. When gene expression in wild type and the clp mutants, at 30° C., were compared, the clpE mutant exhibited almost the same expression pattern as that of the wild type for cbpA, ply, psaA, and cps2A, whereas the clpP⁻ mutant showed increased expression of cbpA but decreased expression of ply and psaA. Thus, clpP seems to act as a negative regulator for cbpA expression, but as a positive regulator for ply expression. Contrary to our observation, Chastanet et al. (Chastanet, A. et al., 2001. Regulation of *Streptococcus pneumoniae* clp genes and their role in competence development and stress survival. J. Bacteriol. 183:

7295-7307) reported that Ply production was not affected by clpP mutation. This discrepancy might be due to a difference in measurement method for Ply activity, as they assessed this qualitatively by observing hemolytic halos on blood agar plates, whereas we employed a quantitative hemolysis assay. Since Ply is a proven virulence factor in pneumococcal bacteremia, increased expression after heat shock may be a contributing factor in pathogenesis. This is the first report of regulation of virulence genes by heat shock in the respiratory pathogen *S. pneumoniae.*

After heat shock, real-time RT-PCR data demonstrated an increase in ply expression in the clpP⁻ mutant, whereas immunoblot analysis and Ply activity measurements revealed no increase. This inconsistency could be attributed to instability of ply mRNA at high temperatures in the clpP⁻ mutant. It is also conceivable that ClpP might act in activating nascent Ply directly. Our immunoblot data also demonstrated that clpP⁻ mutation resulted in high level expression of ClpL regardless of heat shock, suggesting that ClpP may negatively regulate ClpL. This result corroborates a recent microarray study which also showed high induction of clpL at 37° C. in a clpP⁻ mutant (Robertson, G. T. et al., 2002. Global transcriptional analysis of clpP mutations of type 2 *Streptococcus pneumoniae* and their effects on physiology and virulence. J. Bacteriol. 184:3508-3520). Additionally, after heat shock, the level of expression of cps2A, the first gene in the capsule biosynthesis locus, was reduced in the wild type and clpL⁻ mutant, implying potentially lower resistance to the host immune system. In contrast, there was no reduction in the level of expression of cps2A in the clpP⁻ mutant. This result suggests that the clpP⁻ mutant ought to exhibit a wild type level of resistance to host macrophages upon stress challenge, even though overall virulence was decreased. This may lead to the establishment of chronic bacteremia, in which the bacteria are able to evade the host immune system and survive in the host but unable to cause fulminant disease, a phenomenon that has been previously demonstrated for a pneumolysin negative mutant of D39.

Taken together, virulence gene regulation could be modulated not only by heat shock but also by ClpL and ClpP proteases. The thermosensitivity of the clpL⁻ mutant as well as refolding activity of denatured rhodanese by the recombinant ClpL provide evidence for a chaperone function of ClpL. Furthermore, clpP was demonstrated to play an essential role in the regulation of ply and cbpA expression.

Example 2

Modulation of Virulence Gene Expression by ClpP and Protective Immunity of ClpP in *Streptococcus pneumoniae*

In this Example, the underlying mechanism by which ClpP attenuates virulence was investigated and it was evaluated whether ClpP immunization could provide protection against the challenge with *S. pneumoniae.*

1. Materials and Methods i) Bacterial Strains, Growth Conditions, and Transformation.

The bacterial strains and plasmid vectors along with new recombinants generated in this study are presented in Table 4. *S. pneumoniae* CP1200, a derivative of Rx-1, was used in this study and was grown in Casitone-Tryptone (CAT) based medium (Supra, Choi et., 1999). *S. pneumoniae* strain D39 (type 2) was grown in Todd Hewitt (THY) broth. For selection of pneumococcal transformants, erythromycin was added to growth medium at a concentration of 0.2 μg/ml. *Escherichia coli* strains (BL21(DE3), DH5α, XL1-Blue indicated in Table 4) were grown in Luria-Bertani (LB) broth or on LB agar. Plasmids were introduced into *E. coli* by transformation as described by Hanahan (Supra, Hanahan, 1983). For selection of *E. coli* transformants, kanamycin (30 μg/ml) was added to the growth medium.

TABLE 4

Bacterial strains and plasmids used in this study.

| Strain or plasmid | Relevant characteristics | Reference or source |
|---|---|---|
| *E. coli* strains | | |
| BL21(DE3) | gal (λcIts857 ind1 Sam7 nin5 lacUV5-T7 gene1) | Novagen |
| DH5α | supE44 ΔlacU169 (ø80 lacZΔM15) | BRL |
| XL1-Blue | relA1 lac [F' proAB lacI$^q$Z ΔM15 Tn10(Tet$^r$)] | Stratagene |
| *S. pneumoniae* strains | | |
| CP1200 | Nonencapsulated derivative of Rx1, malM511 str-1 | Supra, Choi et al., 1983 |
| HYK2 | CP1200, Δ clpP::ermB | Supra, Kwon et al., 2003 |
| D39 | Encapsulated, type 2 | Supra, Avery et al., 1944 |
| HYK302 | D39, Δ clpP::ermB | Supra, Kwon et al., 2003 |
| Plasmids | | |
| PET30 (a) | 5.4-kb, Ap$^r$ | Novagen |

ii) Cell Culture.

Human lung epithelial carcinoma A549 (ATCC CCL-185) and murine macrophage RAW264.7 cells (ATCC TIB-71) were obtained from American Type Culture Collection and cultured at 37° C. and under 5% $CO_2$. The A549 cells were cultured in Dulbecco modified Eagle medium (DMEM) (Gibco BRL, Gaithersburg, Md.) with 4.5 μg/L of glucose, 10% fetal bovine serum (FBS; Gibco BRL, Gaithersburg, Md.), and 100 U/ml of penicillin G and 100 μg/ml of streptomycin. For culturing RAW264.7 cells, RPMI 1640 medium (Gibco BRL, Gaithersburg, Md.) supplemented with 10 mM HEPES, 2 mM L-glutamine, 100 U/ml of penicillin G and 100 μg/ml of streptomycin, and 0.2% $NaHCO_3$ was used as the basic medium and FBS (Gibco BRL, Gaithersburg, Md.) was added at a concentration of 10%.

iii) Preparation of Capsular Polysaccharide (CPS) from Pneumococci.

CPS preparations of D39 and its isogenic ClpP⁻ mutant derivatives were made by resuspending pneumococci ($A_{600}$=0.5) grown on blood agar plates in 150 mM Tris-HCl, pH 7.0; 1 mM $MgSO_4$. This is equivalent to $5\times10^9$ pneumococci/ml. An aliquot of 1 ml was pelleted at 10,000×g. Autolysis of the bacteria was induced by the addition of 0.1% (w/v) sodium deoxycholate (Sigma, St. Louis, Md.) and incubation at 37° C. for 15 min. The samples were then incubated with 100 U mutanolysin (Sigma), 50 μg DNase I (Roche Applied Science, Mannheim, Germany) and 50 μg RNaseA (Roche Applied Science) at 37° C. for 18 h. The samples were then incubated with 50 μg Proteinase K (Sigma) at 56° C. for 4 h prior to storage at −20° C. Subsequently, cellular materials were subjected to immunoblot analysis using polyclonal type 2 polysaccharide specific antiserum.

iv) Antiserum, Gel Electrophoresis, and Immunoblotting.

The preparation of sera against PspA and PdB (toxoid derivatives of Ply) was essentially as described previously (Supra, Ogunniyi A. D., et al., 2000). For immunoblotting, cells were grown in THY until $A_{600}$=0.3, and prepared as described previously (Kwon, H. Y. et al., 2003. Effect of Heat Shock and Mutations in ClpL and ClpP on Virulence Gene Expression in *Streptococcus pneumoniae*. Submitted to Infect. Immun). Sodium dodecyl sulfate polyacrylamide gel electrophoresis (SDS-PAGE, either 10 or 15% polyacrylamide gel) was carried out as described by Laemmli (Laemmli, U. K. 1970. Cleavage of structural proteins during the assembly of the head of bacteriophage T4. Nature 227:680-685). The proteins were electroblotted onto nitrocellulose membrane and then reacted with 1:5000 dilutions of polyclonal mouse antiserum raised against PspA and PdB. For capsule blotting, samples were electroblotted onto nylon membrane, and then reacted with 1:5000 dilutions of ant-serotype 2 polyclonal mouse antiserum. The secondary antibody was a 1:2000 dilution of goat anti-mouse IgG conjugated to alkaline phosphatase (Bio-Rad).

v) Pneumolysin Assay.

Hemolytic activity was determined as previously described (Lock, R. A. et al., 1996. Sequence variation in the *Streptococcus pneumoniae* pneumolysin gene affecting haemolytic activity and electrophoretic mobility of the toxin. Microb. Pathog. 21:71-83) with a minor modification. Briefly, pneumococci grown in THY broth to early-mid log phase ($A_{600}$=0.05-0.1) were harvested by centrifugation at 3900×g for 10 min at 4° C. and resuspended in phosphate buffered saline. Sodium deoxycholate was added to a final concentration of 0.1% and then incubated at 37° C. for 10 min. After centrifugation of the samples, the supernatant was withdrawn and serially diluted. Hemolytic activity was determined by incubation with an equal volume of 1.5% washed human red blood cells (containing 0.001% mercaptoethanol [Merck]) in 96 well microtiter plates at 37° C. for 30 min. Hemolytic titer was determined as the reciprocal of the estimated dilution at which 50% of erythrocytes were lysed at $A_{540}$.

vi) RNA Techniques.

Aliquots of 1.5 ml culture suspension were collected at intervals for extraction of total RNA. For measuring mRNA half-lives, rifampicin (100 μg/ml) was added. Total RNA was extracted using the hot acid phenol method, as described previously (Supra, Ogunniyi A. D., et al., 2002). Levels of mRNA for cps2A and ply, were quantitated by one-step real-time reverse transcription (RT-PCR) using the Promega Access RT-PCR System (Promega Biotech, Cat. # A1250). An internal control primers (16S rRNA) specific for these reactions have been described elsewhere (Supra, Ogunniyi et al., 2002). Preparation of Rt-PCR Reactions, Cycling Conditions and Data Analysis were Substantially the same as described previously (Supra, Kwon et al., 2003). All reactions were carried out in Rotor-Gene 2000 Real-Time cycler (Corbett Research, Australia). The mRNA half-lives were analyzed by SigmaPlot curve fitter program (non-linear least squares fitting to the sum of exponentials). Two models were proposed, a monophasic decay or a biphasic decay. The model which fitted the data with the minimum deviation in each case was retained as being more valid.

vii) Cloning, Expression and Purification of ClpP in *E. coli*.

clpP ORF (Genebank AE008443, base sequences 5416-6006, for which said base sequences 5416 to 6006 of section 59 of 184 of the complete genome are shown in appended SEQ ID NO. 2) was PCR amplified with forward and reverse primers (5'-CGA ATT CAT GAT TCC TGT AGT TAT-3': SEQ ID NO. 11 and 5'-CGA GCT CTT AGT TCA ATG AAT TGT TG-3': SEQ ID NO. 14, which incorporates EcoRI and SacI sites, respectively) from CP1200 DNA. The PCR fragment was digested with the same enzymes and cloned into the corresponding restriction sites of pET30(a) (Novagen) to generate plasmid pET30(a)-clpP (FIG. 1). Expression was induced with 0.1 mM IPTG (isopropyl-R-D-thiogalactopyranoside) in *E. coli* BL21(DE3) for 3 hours. Cells were collected by centrifugation at 6,000 x g for 10 min, and then resuspended in lysis buffer (50 mM Sodium phosphate, pH8.0; 2 M NaCl; 40 mM imidazole) with a protease inhibitor, phenylmethyl-sulfonyl fluoride added to 1 mM of final concentration. Then, cells were lysed in French pressure cell (SLM Aminco, Inc.) at 12,000 $lb/in^2$, and the lysates were centrifuged at 100,000 ×g for 1 hour. The supernatent containing $His_6$-tagged protein was loaded on a nickel-nitrilo-acetic acid column (Probond, InVitrogen), and then was washed with 10 column volumes of 10 mM sodium phosphate, 20 mM imidazole and 1 M NaCl (pH 6.0). Nickel-bound $His_6$-tagged protein was eluted with 30ml of 0 to 500 mM imidazole gradient in 10 mM sodium phosphate buffer (pH 6.0), and dialyzed against 10 mM sodium phosphate buffer (pH 7.0). The protein was >95% pure as judged by SDS-PAGE and staining with Coomassie brilliant blue R250 (data not shown).

viii) Isolation of Subcellular Fractions and Localization.

Exponentially grown cells were collected by centrifugation and sucrose-induced protoplast formation was performed as described previously (Vijayakumar, M. N. et al, 1986. Localization of competence induced proteins in *Streptococcus pneumoniae*. J. Bacteriol. 165:689-695). Cells were converted to protoplasts by incubation at 30° C. for 1 hr with 1 M sucrose buffer (1 M sucrose, 100 mM Tris HCl pH 7.6, 2 mM $MgCl_2$, 1 mM PMSF). Centrifugation at 13,000×g for 20 min separated a cell wall fraction (supernatant) from protoplast (pellet). The protoplasts were subject to osmotic lysis by diluting with 19 volumes of hypotonic buffer (100 mM Tris HCl, pH 7.6, 1 mM PMSF, 1 mM EDTA). Lysates were centrifuged at 5,000×g for 5 min to remove unlysed cells, and then were separated by centrifugation at 50,000×g for 30 min into the cytoplasmic fraction (supernatant) and the membrane fraction (pellet).

ix) Determination of Malate Dehydrogenase Activity.

The enzymatic activity of malate dehydrogenase (MDH) was determined by monitoring the rate of the fall of absorbance of 0.2 mM NADH at 340 nm at 25° C. ($A_{340}$=6.22/mM/cm) in 0.15 M potassium phosphate (pH 7.6) containing 0.5 mM oxalacetate. After adding the sample, the reaction mixtute was incubated at 25° C. for 1 min 40 seconds, and absorbance at 340 nm was determined. Addition of the substrate was used to start the reaction. Initial slope rates of the rate of oxidation of NADH from the first 1 min 40 sec of the reaction were used to calculate MDH activities.

x) Adhesion and Invasion Assay.

Invasion of the human lung A549 cells by pneumococci was performed by a modification of antibiotics protection assay described previously (Supra, Vijayakumar, M. N. et al., 1986). A549 cells were grown to confluence in 24-well tissue culture plates and washed 3 times with phosphate buffered saline (PBS, pH 7.2), and then 1 ml of cell growth medium without antibiotics was added per well. Exponential-phase cultures of R type CP1200 and its isogenic $clpP^-$ mutant strains ($A_{550}$=0.3, $10^8$ CFU/ml) were pelleted by centrifugation, washed once with PBS, and resuspended in DMEM medium. Monolayers were infected with $10^7$ bacteria (bacterium-to-cell ratio, 10:1) and initial contact of the bacteria with the cell monolayer was aided by centrifugation at 800×g for 10 min at 4° C. followed by a 2 h incubation at 37° C. Fresh medium containing 10 μg/ml penicillin and 200 μg/ml gentamicin was added to each well, and such treatment was confirmed to be sufficient to kill all exposed bacteria. After 1 h of further incubation, the monolayers were rinsed 3 times with PBS, and cells were detached from the plate by treatment with 100 μl of 0.25% trypsin-0.02% EDTA and then lysed by the addition of 400 μl of Triton X-100 (0.025% in $H_2O$). Appropriate dilutions were plated on blood agar to determine the number of viable bacteria. To determine the total number of adherent and intracellular bacteria, infected monolayers were washed as described above and then trypsinized, lysed, and plated quantitatively without antibiotic treatment. All samples were assayed in triplicate, and each assay was repeated at least three times.

xi) Survival in RAW264.7 Cells.

Cell monolayers were infected with $10^7$ CFU pneumococci (bacterium-to-cell ratio, 10:1) in RPMI1640 culture medium (Sigma) without antibiotics. For bacterial infection, the culture was incubated for 2 hr at 37° C. After this incubation, the cells were washed three times with PBS, and fresh medium containing 10 μg/ml penicillin and 200 μg/ml gentamicin was added to kill extracellular bacteria (time zero of the assay). To quantify the intracellular pneumococci at different times of postinfection, the supernatants were removed and the cells were washed three times with PBS and then lysed with Triton X-100 as described above. Serial dilutions of lysate from each well were plated onto blood agar. The number of CFU was determined after 24 h incubation at 37° C. Three independent assays (triplicate assay) were carried out for each bacterial strain. Statistical analysis was performed using a paired or unpaired Student's t test.

xii) Study of Colonization.

This study was performed in accordance with the same procedures as described in the recent report (Supra, Ogunniyi et al., 2003, MS in preparation). Prior to challenge, bacteria were cultured at 37° C. overnight on Todd Hewitt agar (Difco Laboratories, USA) with 10% [vol/vol] horse serum added (supplemented with erythromycin where appropriate) and then grown in THY broth for about 4 h at 37° C. to give ca. $4\times10^7$ CFU/ml ($A_{600}$=0.1). Each bacterial culture was then adjusted in THY broth to ca. $10^9$ CFU/ml, and 10 μl of cells (about $10^7$ CFU) were inoculated into the nares of 5 week-old CD1-mouse. 4 mice of each group were randomly sacrificed on day 1, 2, and 4 from post-infection to quantify the carriage of each strain. Samples of nasopharynx, blood and lung were appropriately diluted in sterile PBS in series, and plated in duplicate on blood agar containing proper antibiotic. The plates were incubated under atmosphere of 95% air/5% $CO_2$, at 37° C. for about 16 hrs, and then the colonies were counted and the means of duplicate were obtained.

xiii) Immunization of Mice and Analysis of Sera.

Mice were immunized intraperitoneally as described previously (Supra, Ogunniyi, A. D. et al., 2000). Four groups of 5- to 6-week-old female CBA/N mice (12 mice per group) were immunized intraperitoneally with $AlPO_4$ alone, genetically modified Ply toxoid (PdB)+$AlPO_4$, PspA+$AlPO_4$, or ClpP plus $AlPO_4$. Each mouse received three doses of 10 μg of each protein antigen at 12- to 14-day intervals, and sera were collected from the mice by retro-orbital bleeding 1 week after the third immunization. The sera were pooled on a group-by-group basis and assayed for Ply-, PspA- and ClpP-specific antibodies by enzyme-linked immunosorbent assay (ELISA). The sera were also subjected to Western immonoblot analyses using purified Ply, pspA, or ClpP, or whole-cell lysates of *S. pneumoniae* D39 derivatives as the antigen.

xiv) Challenge.

Two weeks after the last immunization, mice were challenged intraperitoneally with a highly virulent capsular type 2 strain (D39). Before challenge, the bacteria were grown at 37° C. overnight on blood agar and then inoculated into serum broth consisting of 10% (vol/vol) horse serum in meat extract broth (brain heart infusion broth, Difco Laboratories, USA, or Todd Hewitt broth, Difco Laboratories, USA). Bacteria were then grown statically for 3 h at 37° C. to give approximately $10^8$ CFU/ml, and inoculum adjusted to 7.5×105 CFU per challenge dose. Serotype-specific capsule production was confirmed by Quellung reaction using antisera obtained from Statens Seruminstitut, Copenhagen, Denmark. After challenge, the mice were monitored every 4 h initially for 7 days and then daily up to 21 days, and the survival time of each mouse was recorded. Differences between the median survival times of groups were analyzed by the Mann-Whitney U test (one-tailed).

2. Results i) $clpP^-$ Mutant does not Cause Persistant Infection in Mice.

We have shown previously that the $clpP^-$ mutant exhibited significantly attenuated virulence. The level of expression of cps2A, the first gene in the capsule biosynthesis locus, was not reduced in this strain after heat shock whereas expression of cps2A in the parent was significantly reduced after heat shock, suggesting that the $clpP^-$ mutant ought to exhibit a wild type level of resistance to host macrophages upon stress challenge, even though overall virulence was decreased. This may lead to the establishment of chronic bacteremia, in which the bacteria are able to evade the host immune system and survive in the host but unable to cause fulminant disease, a phenomenon that has been demonstrated previously for a pneumolysin negative mutant of D39.

To confirm this hypothesis, 10 mice were injected with $10^5$ cfu of the $clpP^-$ mutant intraperitoneally and blood was taken from retro-orbitally after infection. The result showed that pneumococci were not detected in any mice 7, 14, and 21 days from post-infection, indicating that the $clpP^-$ mutation does not cause persistent infection (data not shown).

ii) Determination of mRNA Half-lives.

We recently demonstrated that in the $clpP^-$ mutant, there was an increase in ply mRNA expression with no concomitant increase in Ply protein and Ply hemolytic activity after heat shock. However, in the wild type, both Ply protein and hemolytic activity levels as well as ply mRNA level were increased significantly after heat shock (Supra, Kwon H.Y. et. al, 2003).

Figure 11A:
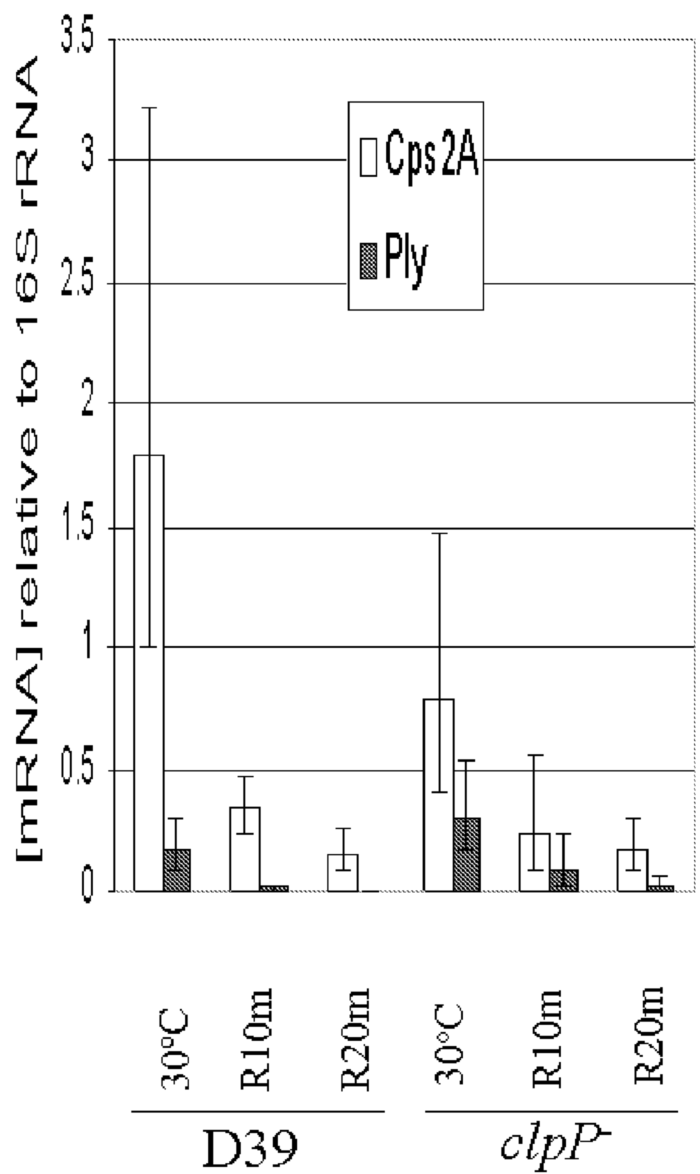
FIGS. 11*a* to 11*c* show detection of relative mRNA stabilities of cps2A, and ply by real-time RT-PCR.
Figure 11B:
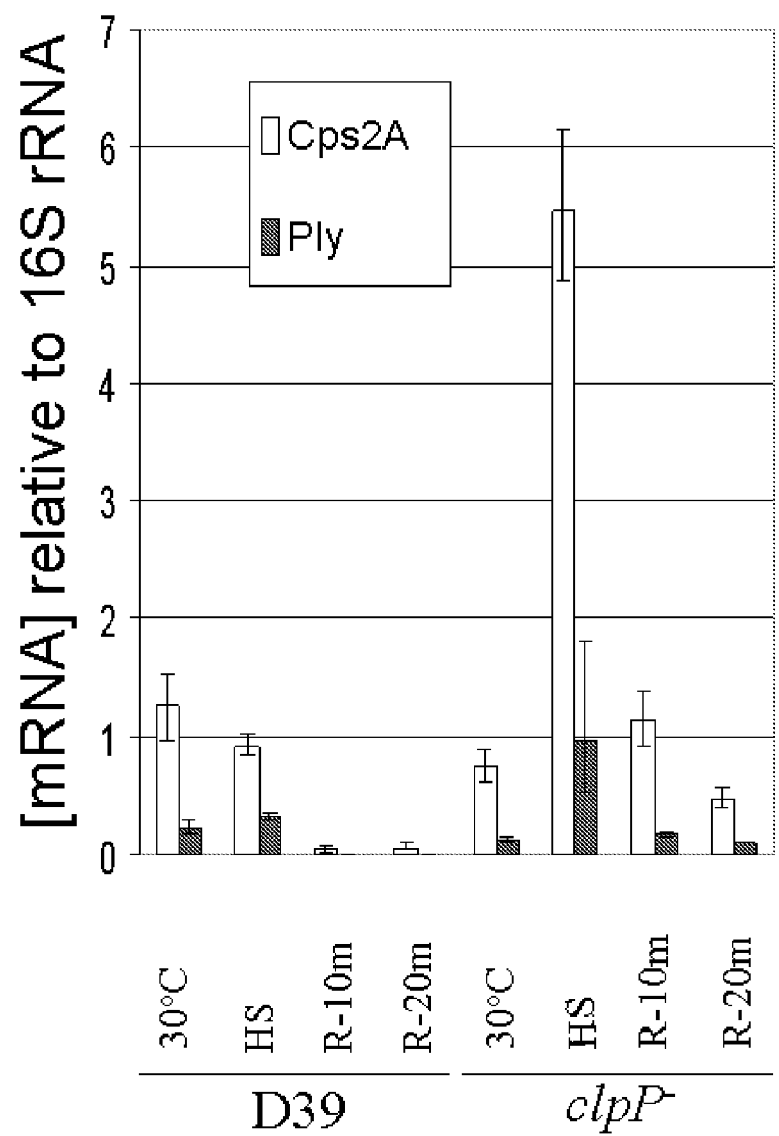
Figure 11C:
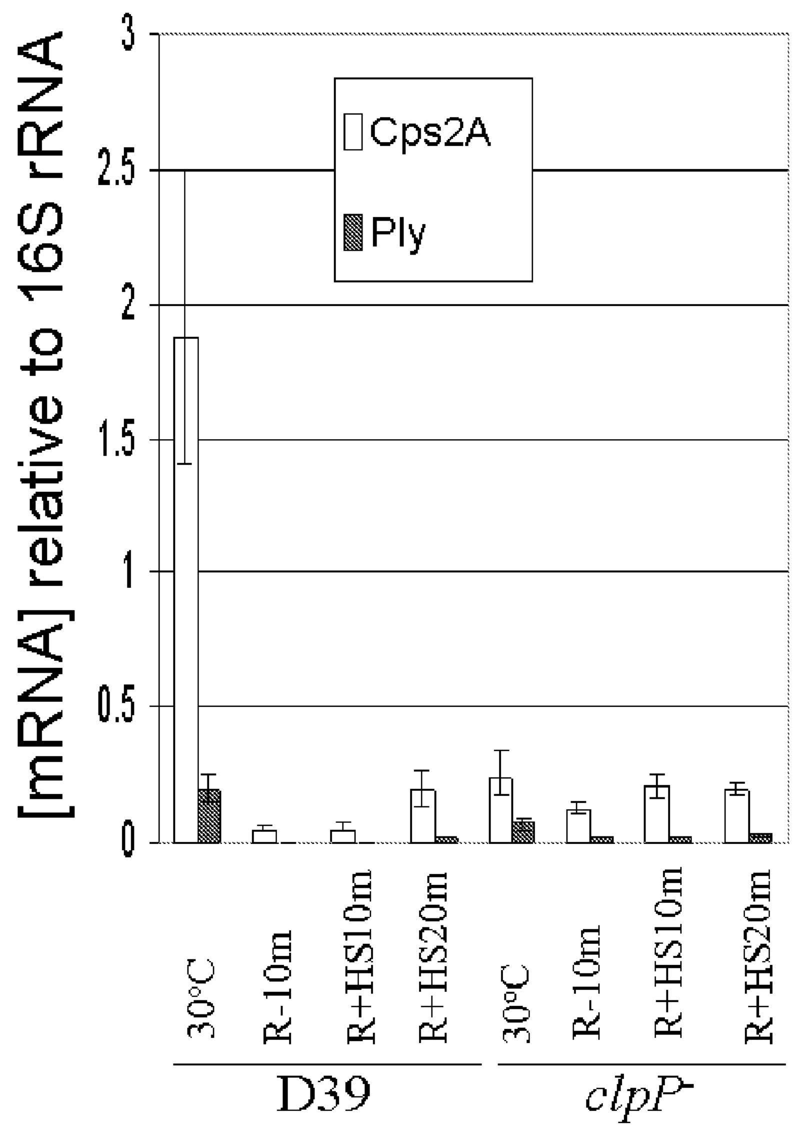

This inconsistency could be attributed to instability of ply mRNA at high temperatures in the $clpP^-$ mutant. Therefore, the ply mRNA decay kinetics after heat shock (HS) was investigated. To compare the stability of the mRNA at 30° C., de novo mRNA synthesis was blocked by the addition of rifampicin and the decay was monitored by real-time RT-PCR using the cps2A and ply specific primers (FIG. 11*a*). To determine mRNA half-lives at 30° C., *S. pneumoniae* strains were first grown at 30° C., then rifampicin was added. Aliquots for RNA extraction were withdrawn before the addition of rifampicin (30° C.) and at 10 (R10m) and 20 min (R20m) after rifampicin was added (FIG. 11*a*). To determine mRNA half-lives after heat shock, *S. pneumoniae* strains were first grown at 30° C. and then heat shocked at 42° C. Ten minutes later at 42° C., rifampicin was added (HS). Aliquots for RNA extraction were withdrawn before and after heat shock, and at 10 (R-10m) and 20 min (R-20m) after the addition of rifampicin at 42° C. (FIG. 11*b*). To determine effect of heat shock on mRNA half-lives, *S. pneumoniae* strains grown at 30° C. were treated with rifampicin for 10 min, and then heat shocked at 42° C. Aliquots for RNA extraction were withdrawn before, and 10 min (R-10m) after the addition of rifampicin at 30° C., and then at 10 (R+HS10m) and 20 min (R+HS10m) after heat shock (FIG. 11*c*). Between RNA extracts, levels of individual mRNA species were corrected with reference to that obtained for the internal 16S rRNA control. Data points represent means±standard deviations of quadruplicate samples from each RNA extract. Comparison of the degradation kinetics demonstrated that at 30° C., the half-life of ply mRNA in the wild and the clpP mutant were 2.75 and 5.8 min, respectively, indicating that the half-life of ply in the mutant was 2.1-fold higher than that of the wild type at 30° C. (Table 5). However, at 30° C., degradation of the cps2A mRNA in the clpP$^-$ mutant was only 1.31-fold higher than that of the parent (FIG. 11*a* and Table 5). This result suggests that ClpP protease could be responsible for the degradation of cps2A and ply mRNA at 30° C. in some unknown way.

TABLE 5

Effect of heat shock on half-lives of cps2A and ply mRNA[a].

| | Half-life, min | | | |
|---|---|---|---|---|
| | D39 | | clpP$^-$ | |
| Temperatures | cps2A | Ply | Cps2A | ply |
| 30° C. | 3.8 | 2.75 | 5.0 | 5.8 |
| 42° C. | 2.0 | 1.75 | 4.1 | 3.75 |

For measuring mRNA half-lives, rifampicin (100 μg/ml) was added and aliquots of 1.5 ml culture suspension were collected at 10 min intervals, and total RNA was extracted using the hot acid phenol method. Subsequently, mRNA levels were determined by real-time RT-PCR. The mRNA half-lives were analyzed by non-linear least squares fitting to the sum of exponentials. All experiments were carried out in quadruplicate. To compare the stabilities of the transcripts after heat shock, *S. pneumoniae* cells were first grown at 30° C., then shifted to 42° C. Total RNA was prepared immediately before the addition of rifampicin at 42° C. as well as at 10 and 20 min after adding rifampicin at 42° C. After heat shock, the level of ply mRNA in the clpP$^-$ mutant was increased 7.5-fold (FIG. 11*b*) but the level of Ply protein was not increased (data not shown), corroborating our previous results. The decay kinetic data showed that the half-lives of the ply transcripts in the parent and clpP$^-$ mutant were 1.75 and 3.75 min, respectively, indicating that ply mRNA in the clpP$^-$ mutant was degraded 2.1-fold slower than that of the parent after heat shock. Furthermore, the half-lives of cps2A transcripts in the parent and clpP$^-$ mutant were 2.0 and 4.1 min, respectively, indicating that the cps2A mRNA in the clpP$^-$ mutant was degraded 2.05-fold slower than that of the parent after heat shock (FIG. 11*b*).

Given that after heat shock, half-lives of the ply and cps2A mRNA transcripts became shorter than those at 30° C. in both the parent and clpP$^-$ mutant, it is possible that the mRNA species are either liable to faster degradation at 42° C. relative to 16S rRNA or subject to faster decay by HSPs other than ClpP. Therefore, we investigated whether heat shock itself could affect half-life of ply mRNA. To resolve the effect of heat shock on ply mRNA half-life, cells cultured at 30° C. were treated with rifampicin, then heat shocked, and the decay kinetics of the mRNA was determined by RT-PCR analysis. Under these conditions, both cps2A and ply transcripts were stable over 20 min in the parent and the clpP$^-$ mutant (FIG. 11*c*), which was in contrast to the scenario observed at 30° C. (see FIG. 11*a*). This result demonstrated that the transcripts are indeed stabilized by heat shock at 42° C. (FIG. 11*c*).

iii) The Hemolytic Activity of Ply is not Activated by ClpP.

The destabilizing function of ClpP could be responsible for the low stability of the ply processing product and of the ply primary transcript. Even though the ply mRNA was stabilized by heat shock, there was no corresponding increase in the amount of Ply protein or the level of its hemolytic activity. This discrepancy could be attributed to the activation of Ply directly by ClpP protease so that hemolytic activity could be increased in the parent but not in the clpP$^-$ mutant.

To prove this hypothesis, *S. pneumoniae* cells were cultured at 30° C. and then heat shocked at 42° C. for 20 min. The cells were lysed with 0.1% sodium deoxycholate by incubation at 37° C. for 10 min. Subsequently, cell lysates were incubated further at 37° C. for 20, 40, and 60 min, and the hemolytic activity of Ply was determined. The hemolytic activities in both wild type and the clpP$^-$ mutant decreased over the period and hemolytic titer at 37° C. in the clpP$^-$ mutant was not significantly different from that in the parent, suggesting that ClpP protease is not required for the activation of hemolytic activity of Ply (data not shown).

iv) Translocation of ClpP to the Cell Wall after Heat Shock.

Localization of hsp100 with immunogold labeling employing anti-hsp100 antibody showed that hsp100 was located in the cytoplasm and nucleus before and after heat-shock in the yeast *Saccharomyces cerevisiae* (Fujita et al., 1998. Hsp104 responds to heat and oxidative stress with different intracellular localization in *Saccharomyces cerevisiae*. Biochem. Biophys. Res. Commun. 248: 542-547). In *B. subtilis*, immunogold labeling with antibodies revealed that ClpC and ClpX ATPases were detected at the cell envelope as well as inside the cells (Kruger, E. et al., 2000. The clp proteases of *Bacillus subtilis* are directly involved in degradation of misfolded proteins. J. Bacteriol. 182: 3259-3265) suggesting that hsp100, ClpC, and ClpX proteins are associated closely with protein aggregates during heat-shock treatment.

To localize ClpP in *S. pneumoniae*, fractionation of subcellular proteins was initially attempted using encapsulated strains. However, after incubation of the cells in 1 M sucrose buffer, centrifugation did not separate the cell wall from protoplast due to the presence of a thick capsule (data not shown). Therefore, non-encapsulated strains were used for localization experiments. Since the fractionation method may cause partial lysis or leakage of cytoplasmic contents during or after heat shock, MDH was used as an internal cytoplasmic marker. MDH activity in the cell wall was <10% of the total MDH activity at 30° C. (data not shown). In addition, MDH activity in the cell wall was not increased even after heat shock (data not shown), suggesting that heat shock does not cause lysis or leakage of cell membrane.

Exponentially grown *S. pneumoniae* CP1200 cells were exposed to 42° C., and cellular proteins were fractionated into cell wall, membrane, and cytoplasm by sucrose-induced protoplast formation followed by lysis in hypotonic buffer (see Materials and Methods). Subsequently, subcellular fractions were subjected to immunoblot analysis using polyclonal anti-ClpP antibody (obtained by subcutaneously injecting a rabbit with mix of ClpP protein and alum 3 times at 2-week interval, and then taking the serum from the rabbit) to visualize the ClpP. ClpP was detected predominantly in the cytoplasmic fraction but lesser amount in the cell wall fraction at 30° C.

Figure 14:
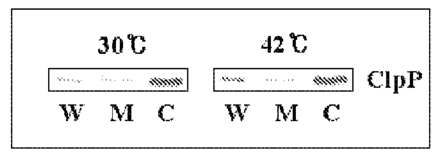
FIG. 14 shows translocation of ClpP after heat shock.

However, after heat shock, the amount of ClpP in both the cytoplasm and cell wall was increased (FIG. 14) indicating that ClpP is induced at normal temperature but it is further induced after heat shock. In FIG. 14, W, M, and C mean cell wall, membrane, and cytoplasm, respectively. This result suggests that a significant amount of ClpP may be translocated to the cell wall after heat shock, thus ClpP might play some important role in the cell wall or perhaps be involved in degradation of proteins.

v) Results of Colonization or Lung Invasion of the clpP$^-$ Mutant.

It was shown previously that the clpP$^-$ mutant exhibited strong attenuation of virulence in murine septicemia model (Supra, Kwon H. Y. et al., 2003). Moreover, the clpP$^-$ mutant failed to colonize the lungs of mice to significant levels after intratracheal challenge and no mortality was recorded throughout the 48 hr of infection (Supra, Robertson, G. T. et al., 2002). However, invasion and dissemination of *S. pneumoniae* seem to be accomplished via its natural niche, nasopharynx.

Figure 12A:
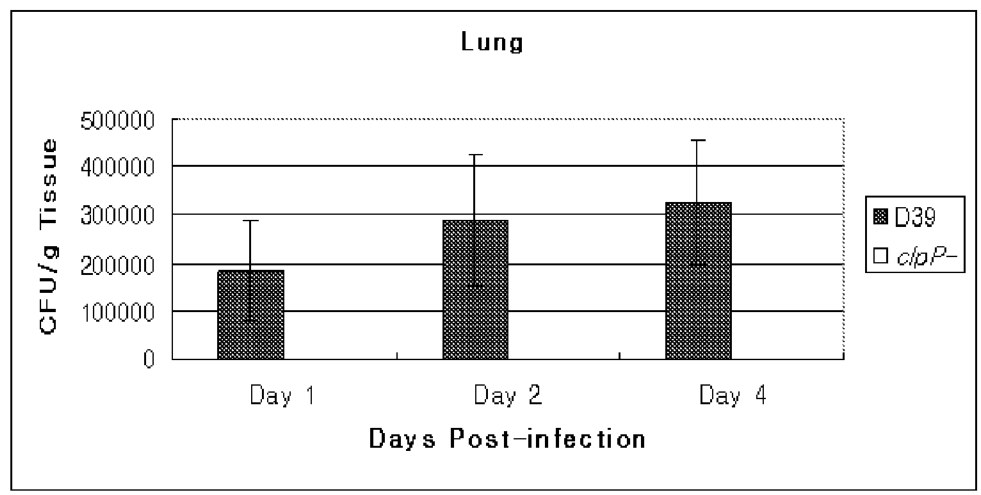
FIGS. 12*a* to 12*c* show evaluation of bacteria recovery from nasopharynx of CD1 mice during 4 days after intranasal challenge with D39 and its isogenic clpP$^-$ derivative. The values are means±standard deviations of means at each point (n=5).
Figure 12B:
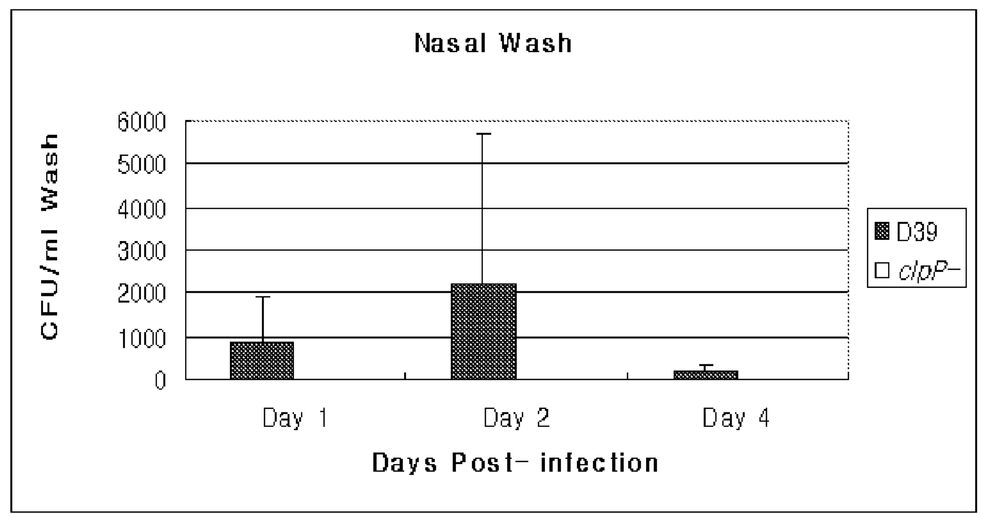
Figure 12C:
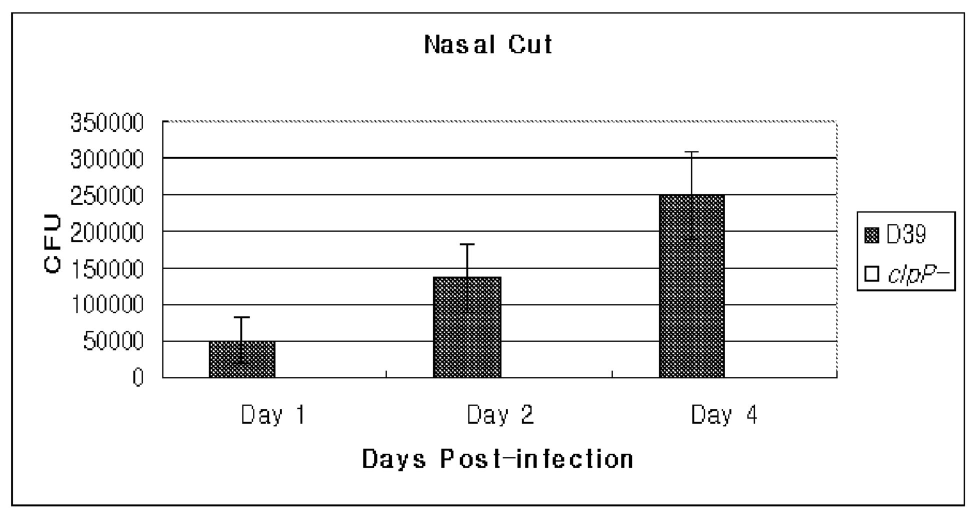

Therefore, the effect of ClpP on colonization of *S. pneumoniae* after intranasal challenge was assessed. Intranasal challenge with a highly virulent capsular type 2 strain (D39) and its isogenic clpP$^-$ mutant (HYK302) revealed that the clpP$^-$ mutant did not colonize the nasal mucosa and lung at all throughout the 48 hr period (FIGS. 12*a* to 12*c*), suggesting a defect in adherence.

Furthermore, ClpC of *S. pneumoniae* has been shown to be involved in adherence (Charpentier, E., R. Novak, and E. Tuomanen. 2000. Regulation of growth inhibition at high temperature, autolysis, transformation and adherence in *Streptococcus pneumoniae* by clpC. Mol. Microbiol. 37:717-726), and mutations in clpC (Rouquette, C., C. de Chastellier, S, Nair, and P. Berche. 1998. The ClpC ATPase of *Listeria monocytogenes* is a general stress protein required for virulence and promoting early bacterial escape from the phagosome of macrophages. Mol. Microbiol. 27: 1235-1245), clpE (Nair, S., C. Frehel, L. Nguyen, V. Escuyer, and P. Berche. 1999. ClpE, a novel member of the HSP100 family, is involved in cell division and virulence of *Listeria monocytogenes*. Mol. Microbiol. 31: 185-196), and clpP (Supra, Pederson, K. J., et al., 1997) in *Listeria* and *Yersinia* showed decrease in adherence to host epithelial cells.

Therefore, the involvement of ClpP in adherence to host epithelial cells was examined. Since the presence of polysaccharide capsule significantly attenuates adherence of pneumococcus to the surface of host cells, we employed R type strains to determine effect of clpP$^-$ mutation on adherence and invasion. The R type clpP deletion mutant, HYK2, did not show any significant differences in adherence to and invasion of A549 human lung cells compared to that of its isogenic parent (data not shown). Thus, this result demonstrates that colonization failure was not due to the defect in adhesion nor invasion.

vi) Reduced Survival of the clpP$^-$ Mutant in Murine Macrophage RAW264.7 Cell Line.

Alveolar macrophage is the primary element in host defense against invasion by *S. pneumoniae* (Knapp, S. et al., 2003. Alveolar macrophages have a protective antiinflammatory role during murine pneumococcal pneumonia. Am. J. Respir. Crit. Care Med. 167:171-179). Since it was observed in this study that the clpP$^-$ mutant was defective in colonization of the nasal mucosa compared to the parent, it was reasoned that this quite possibly was due to rapid clearance of the pneumoccoci in addition to the slower growth of the mutant.

Figure 13:
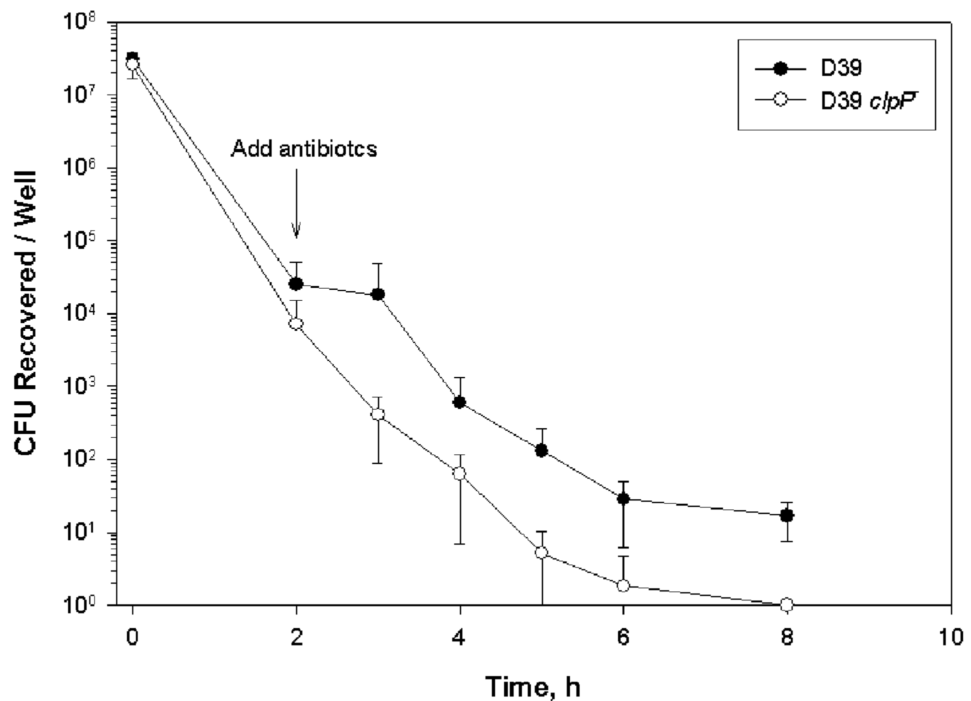
FIG. 13 shows survival of the clpP$^-$ mutant in macrophage cells.

Therefore, the survival of the clpP$^-$ mutant was determined in murine macrophage RAW264.7 cells (FIG. 13). RAW264.7 cell monolayers were infected with $10^7$ CFU pneumococci (bacterium-to-cell ratio, 10:1) in RPMI1640 culture medium, and were treated with gentamicin at different time, and then intracellular pneumococci were quantified. Three independent assays were carried out in triplicate for each bacterial strain. The D39 parent strain was able to survive inside the macrophages and was maintained at a level of 160 CFU during the course of the assay (8 h), whereas the number of recoverable clpP$^-$ mutant organisms declined steadily to zero after 8 h of infection (FIG. 13). The survival rate of ClpP$^-$ mutants in the macrophage cells was significantly decreased at 5 hr ($P<0.01$), 6 hr ($P<0.05$), 8 hr ($P<0.01$) from post-infection as compared with its parent strain (FIG. 13). The number of viable cells at 2 hr after the addition of antibiotic would be approximately half the number present at the time the antibiotic was added. However, the actual number of CFU was much less than what was estimated, indicating that it is not a growth defect of the clpP$^-$ mutant but rather a result of stress-sensitive phenotype or susceptibility of the clpP$^-$ mutant to macrophage. This suggests that ClpP is required for intracellular survival in the RAW264.7 cells.

vii) Level of cps in clpP$^-$ Mutant is Similar to that of the Wild Type Strain.

In clpP$^-$ mutant derivatives of *Streptococcus mutans* and *Pseudomonas fluorescence*, biofilm level was reduced significantly (Lemos, J. A., and R. A. Burne. 2002. Regulation and physiological significance of ClpC and ClpP in *Streptococcus mutans*. J. Bacteriol. 184:6357-6366). Accordingly, the amount of cps in those mutants was considered to be lower than that of the parental type.

To examine if this also holds true for *S. pneumoniae*, D39 and its isogenic clpP$^-$ mutant derivative were used to measure the amount of cps by immunoblot analysis using polyclonal type 2 polysaccharide specific antiserum. Both cultures were adjusted to the same optical density to exclude the possibility that any differences observed could be due to variations in the growth capacity of the strains. In both the parent (D39) and the clpP$^-$ mutant (HYK302), the same amount of cps was detected (data not shown) indicating that the attenuation of virulence in the clpP$^-$ mutant was not due to lower level of cps.

viii) Protective Effect of ClpP Against Pneumococcal Challenge in Mice.

HSPs serve as antigens in some pathogens and they serve to protect against infectious diseases. Since ClpP is translocated into the cell wall after heat shock, its ability to elicit protection against pneumococcal challenge was evaluated.

Figure 15A:
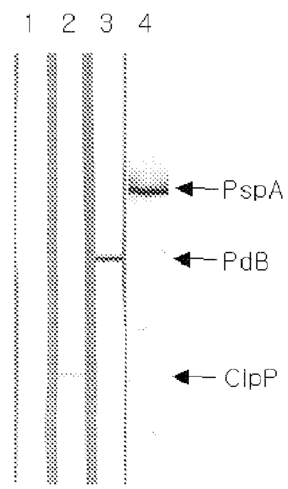
FIGS. 15*a* and 15*b* show Western immunoblot analysis of whole-cell lysates of *S. pneumoniae* D39 (FIG. 15*a*) and of purified PdB (53 kDa), PspA fragment (43 kDa) and ClpP (21 kDa) (FIG. 15*b*), showing specificity of antibody responses to the protein antigens.
Figure 15B:
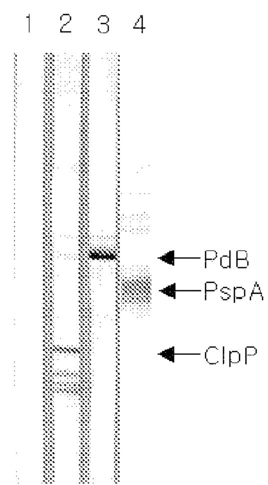

The proteins separated by SDS-PAGE were electroblotted onto nitrocellulose membrane. They were then reacted with sera from the groups of mice immunized with the proteins. The results were shown in FIGS. 15*a* and 15*b*. In FIGS. 15*a* and 15*b*, nitrocellulose membrane strips in Lanes 1 to 4 were reacted with sera from mice immunized with $AlPO_4$ adjuvant (lane 1), PdB plus $AlPO_4$ (lane 2), PspA plus $AlPO_4$ (lane 3), and ClpP plus $AlPO_4$ (lane 4). Mice immunized with ClpP elicited strong, specific antibody response to the antigen; ELISA titer of pooled sera from mice immunized with purified ClpP was 8,400±2250 compared to the titer obtained from mice immunized with purified PdB (8,000±600) and PspA (8,300±2,400). Mice immunized with alum ($AlPO_4$) adjuvant alone produced a titer of 100, which was the limit of detection. Western immunoblot of the sera against whole-cell lysates of D39 also demonstrated specificity of antibody responses to each of the antigens (FIG. 15*a*). The sera also reacted specifically to each of the purified proteins (FIG.

15*b*). However, in case of the purified ClpP, some degradation products of the protein were observed.

Figure 16:
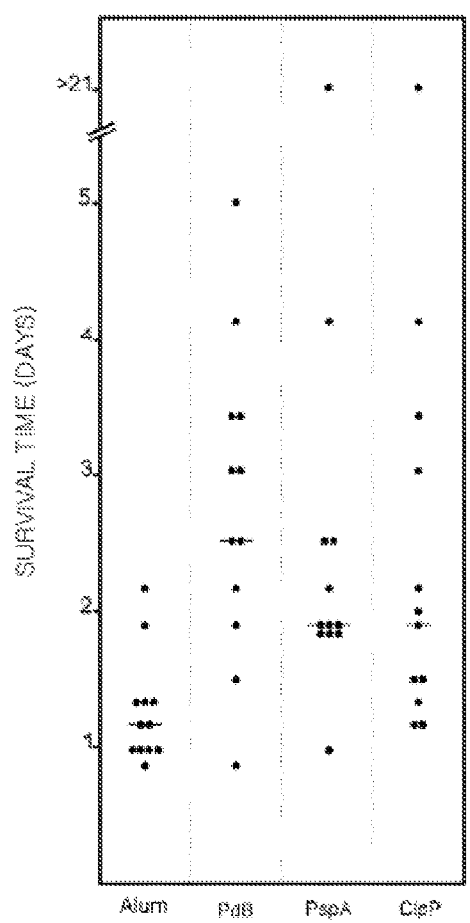
FIG. 16 shows survival times of mice challenged with virulent strain D39 after the third immunization with ClpP and other known antigen proteins.

In the active immunization/challenge experiment, mice were challenged with ca. $7\times10^5$ CFU of D39. Groups of 2 CBA/N mice were immunized with the indicated antigens and were challenged 2 weeks after the third immunization with approximately $7.5\times10^5$ CFU of capsular type 2 strain D39. The results were shown in FIG. 16. In FIG. 16, each datum point represents one mouse, and the horizontal lines denote the median survival time for each group. The median survival time for mice that received ClpP was approximately 2 days (FIG. 16). This was significantly longer than that for mice that received the alum adjuvant alone ($P<0.01$). Similarly, the median survival time for mice that received PspA (2 days) was significantly longer than that for mice that received the alum adjuvant alone ($P<0.001$). For mice that received PdB (the pneumolysin toxoid), the median survival time was approximately 2.5 days and this was also significantly longer than that for mice that received the alum adjuvant alone ($P<0.001$). However, when the median survival time for mice that received ClpP was compared to that obtained with either PdB or PspA, no significant differences were obtained.

3. Discussion

The aim of this study was to evaluate the role of ClpP, a heat shock protein, in the pathogenesis of pneumococcal disease. We have demonstrated, after heat shock in the $clpP^-$ mutant, an increase in ply mRNA whereas no increase of both Ply protein level and Ply hemolytic activity. This inconsistency turned out that the ply and cps2A mRNA in the $clpP^-$ mutant became stable in the $clpP^-$ mutant at both 30° C. and 42° C., thus ClpP seems to be a contributing factor for decay of the transcripts. Furthermore, after heat shock, half-lives of both cps2A and ply mRNA in the $clpP^-$ mutant were more than two-fold longer than those in the wild type indicating clearly that lack of ClpP elicited increase of half-lives of the mRNA species after heat shock. The hemolytic activity of Ply was not increased further by incubation of the cell lysate at 37° C., indicating that ClpP is not directly responsible for activation of hemolytic activity of Ply. We concluded from these findings that cps2A and ply mRNA are subject to ClpP degradation at posttranscriptional level but the specific mechanism by which this occurs is yet unclear.

In *S. pneumoniae*, cps is a key virulence factor and provides resistance to phagocytosis (Austrian, R. 1981. Some observations on the pneumococcus and on the current status of pneumococcal disease and its prevention. Rev. Infect. Dis. 3(Suppl.): S1-S17). Whereas in *S. mutans*, $clpP^-$ mutation resulted in 80% reduction in biofilm formation (Lemos, J. A., and R. A. Burne. 2002. Regulation and physiological significance of ClpC and ClpP in *Streptococcus mutans*. J. Bacteriol. 184:6357-6366), the amount of cps in the $clpP^-$ mutant of *S. pneumoniae* is the same as that of the wild type. Therefore, the reduced survival of the $clpP^-$ mutant in macrophage and its failure to colonize the nasal mucosa seem not to be due to the level of cps but rather due to impaired growth at both 30° C. and 37° C. (Supra, Kwon H. Y. et al., 2003). This could also be due to its stress sensitive phenotype, resulting from the accumulation of denatured proteins that are normally targeted to the ClpP protease. In some pathogens, HSPs are present on the surface of cells and may mediate adhesion to the host cells (Marcellaro et., 1998). In *S. pneumoniae* (Supra, Charpentier E. et al., 2000) and *L. monocytogenes* (Nair, S., E. Milohanic, and P. Berche. 2000. ClpC ATPase is required for cell adhesion and invasion of *Listeria monocytogenes*. Infect. Immun. 68: 7061-7068), ClpC was required for cell adhesion and expression of virulence factors; *S. pneumoniae* clpC mutant displayed deficiency in adherence to the human type II alveolar cells and did not express pneumolysin and the choline-binding proteins, CbpA, CbpE, CbpF, or CbpJ, suggesting that the heat shock protein ClpC plays a pleiotropic role in adherence (Supra, Charpentier et al., 2000). In this study, we demonstrated that adherence and invasion of $clpP^-$ mutant of *S. pneumoniae* to the host cells were not affected (data not shown). This could be ascribed to a counter action in expression of proteins such as CbpA and PsaA. After heat shock, expression of CbpA increased whereas expression of PsaA decreased significantly at both mRNA and protein levels (Supra, Kwon et al.) in the $clpP^-$ mutant resulting in no net change in adherence.

Molecular chaperones of the hsp70 and hsp100 family have been shown to be associated with the translocation complex, and they interact with translocation precursors (Berry, A. M. et al., 1989. Reduced virulence of a defined pneumolysin negative mutant of *Streptococcus pneumoniae*. Infect. Immun. 57:2037-2042; Supra Vijayakumar, M. N. et al., 1986). Recently, *B. subtilis* ClpC and ClpX ATPases were detected at the cell envelope and cytoplasm (Supra, Kruger, E. et al., 2000). In those studies, translocation of the Clp protein itself after heat shock or by other stresses was not demonstrated. However, biochemical fractionation of *S. pneumoniae* revealed substantial increase in the amount of ClpP in the cell wall fraction after heat shock. Thus, ClpP is the first Clp protein shown to be mobilized into the cell wall fraction after heat shock, where it interacts with host cells or otherwise acts by degrading pneumococcal proteins destined for transport/translocation.

Bacterial HSP is induced during infection and mediates adhesion and invasion besides its proper folding of intracellular proteins (Supra Charpentier et al., 2000; Supra Nair et al., 2000; Parsons, L. M. et al., 1997. Alterations in levels of DnaK and GroEL result in diminished survival and adherence of stressed *Haemophilus ducreyi*. Infect. Immun. 65:2413-2419). In this work, we demonstrated that immunization of mice with purified pneumococcal ClpP prior to challenge with virulent D39 elicited protective immunity against systemic disease to a level comparable to that obtained with the well-characterized pneumococcal protein vaccine candidates, PspA and Ply. The fact that strong, antigen-specific antibody responses were generated in immunized mice prior to challenge suggests that the protection could at least in part, be antibody-mediated. In conclusion, the expression of cps2A and ply could be mediated by ClpP at the posttranscriptional level. ClpP was translocated into the cell wall after heat shock, and immunization of mice with the purified protein prior to virulent *S. pneumoniae* challenge provided protective immunity against systemic disease.

Example 3

Study of ClpP of *S. pneumoniae* and Human ClpP Responses i) Bacterial Strains and Culture

*S. pneumoniae* CP1200 strain (R type), which has no capsular polysaccharide and is non-pathogenic (Supra, Choi et. al., 1999), was grown in CAT based medium (Casitone 1%, Tryptone 0.5%, NaCl 0.5%, Yeast Extract 0.1%, 0.175M $K_2HPO_4$, and glucose 0.2%), and pathogenic *S. pneumoniae* strain D39 with capsular polysaccharide (type 2; Avery, O. T., et al., 1944. Studies on the chemical nature of the substance inducing transformation of pneumococcal types. Induction of transformation by a desoxyribonucleic acid fraction isolated from pneumococcus type III. J. Exp. Med. 79:137-158) and clinically isolated strain Spn1049 (*S. pneumoniae* isolated from patients in Samsung Medical Center, Korea, which is sensitive to Optochin and bile acid, and shows incomplete hemolytic response on blood-agar medium) were grown in Todd Hewitt broth with 0.5% yeast extract added. *Saccharomyces cerevisiae* (ATCC 287) was grown in YNB medium (Difco Laboratories, USA) containing 2% glucose, *Streptococcus thermophilus* (KCTC 3778) was grown in MRS medium (Difco Laboratories, USA), *Bacillus subtilis* Marburg strain (Boylan S A, Chun K T, Edson B A, Price C W. Early-blocked sporulation mutations alter expression of enzymes under carbon control in *Bacillus subtilis*. Mol Gen Genet. 212(2):271-280 (1988)), *Pseudomonas aeruginosa* (ATCC 15522), *Salmonella typhi* (ATCC 27870), and *E. coli* DH5α (Bethesda Research Laboratory) were grown in Nutrient medium (Difco Laboratories, USA), and human lung cancer A549 cell line (ATCC CCL 185) was grown in DMEM medium (Gibco BRL) containing 10% FBS and 2% penicillin streptomycin.

ii) Immunoblot Analysis

Immunoblot with anti-ClpP antibody was performed to identify the similarity of ClpP of *S. pneumoniae* to other organism derived proteins. The lysates of *S. pneumoniae* and different organisms were subject to 10% polyacrylamide gel electrophoresis, transferred onto nitrocellulose membrane, then immunoblotted with anti-ClpP antibody, and then screened with enzyme-labeled secondary antibody. In other words, nitrocellulose membrane was treated with Tris-buffered saline (TBS) (50 mM Tris, 150 mM NaCl, pH 7.2) solution containing 2% Tween 20 to block non-specific antigen-antibody response, and then slowly shaken at room temperature for 1 hour, for reaction with rabbit anti-ClpP antiserum in TBS solution containing 0.05% Tween 20. A 1:1000 dilution of HRP (Horse raddish peroxidase)-conjugated goat anti-rabbit immunoglobulin G (IgG) antibody in TBS solution containing 0.05% Tween 20 was used as secondary antibody, and hydrogen peroxide and 95% ethanol-solublized —N',N',N',N tetramethyl benzidine were used as a substrate and a color developer, respectively.

iii) Comparison of Amino Acid Sequences of ClpP Proteins

The genes contiguous with *S. pneumoniae* ClpP were identified and also the similarity with other organism-derived ClpP proteins were identified by using BLAST analysis provided by National Center of Biotechnology Information (NCBI, U.S.A.). BLAST analysis showed that amino acid sequence deduced from base sequence of *S. pneumoniae* ClpP has a high similarity to that of the other organism-derived ClpP. In particular, *S. pneumoniae* ClpP showed 88% and 87% identity and 91% and 92% similarity with ClpP proteins of *Streptococcus salivarius* and *Streptococcus agalactiae*, respectively. Also, it showed 89% similarity with *L. Lactis* ClpP, 81% similarity with *Enterococcus faecalis* ClpP, 79% similarity with *Staphylococcus aureus* ClpP, and 75% similarity with *B. subtilis*. Particulary, it showed 70% similarity with *Homo sapiens*. A comparative analysis of the amino acid sequence of clpP proteins showed that in overall, the ClpP proteins have high similarities, in particular, residue parts of serine-96, histidine-121, and aspartate-172, which are deduced as active sites of serine protease, have very high conservation.

iv) Similarity of ClpP of *S. pneumoniae* to Other ClpP Members

Figure 17A:
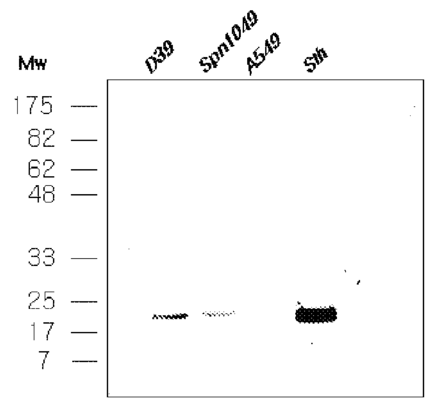
FIGS. 17*a* and 17*b* show immunoblot results indicating anti-ClpP antibody responses to proteins derived from other organisms (The numbers in the left of the Figure represent molecular weights of proteins, and *S. pneumoniae* D39 and Spn1049 represent *S. pneumoniae* D39 and clinical strain 1049, respectively. Sth represents *Streptococcus thermophilus*, A549 represents human lung cancer A549 cell line, Sce represents *Saccharomyces cerevisiae*, Bsu represents *Bacillus subtilis*, Pae represents *Pseudomonas aeruginosa*, Eco represents *E. coli*, Sty represents *Salmonella typhi*).
Figure 17B:
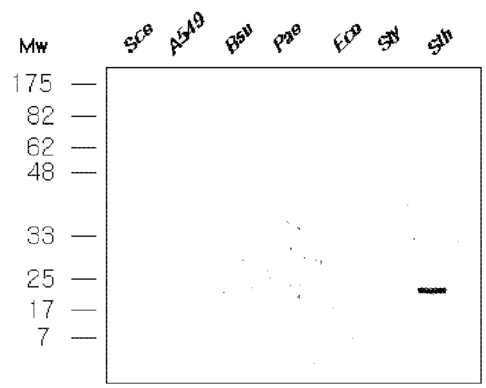

It was previously reported that DnaK of *S. pneumoniae* has a high antigenicity (Hamel, J, Martin D, and Brodeur B B. Heat shock response of *Streptococcus pneumoniae*: identification of immunoreactive stress proteins. Microb. Pathog. 23:11-21 (1997)), and antibody against DnaK of *S. pneumoniae* does not respond to human proteins (Kim S W, Cho I H, Kim S N, Kim Y H, Pyo S N, Rhee D K. Molecular cloning, expression, and characterization of dnaK in *Streptococcus pneumoniae*. FEMS Microbiol Lett. 161(2):217-224 (1998)). Thus, DnaK has been evaluated as a vaccine candidate. Therefore, we investigated whether ClpP has such potential as a vaccine candidate. Immunoblot with cell lysates of other bacteria or higher organisms was performed to identify the simularity of ClpP protein with ClpP family of other organisms. Unexpectedly, anti-ClpP antibody had responses to cell proteins of gram positive bacteria, *Streptococcus thermophilus* (Sth), *S. pneumoniae* D39 (D39) and clinically isolated *S. pneumoniae* strain (Spn1049), but had no responses to *Saccharomyces cerevisiae* (Sce), *B. substilis* (Bsu), *Pseudomonas aeruginosa* (Pae), *Salmonella typhi* (Sty), and human lung cancer cell line A549. These results were shown in FIGS. 17*a* and 17*b*. This suggests that similar to DnaK, ClpP protein of *S. pneumoniae* can be used as a vaccine candidate.

INDUSTRIAL APPLICABILITY

Since vaccine comprising recombinant ClpP protein of *S. pneumoniae* is an antigen protein which has high immunogenicity and is conservatively present in all types of *S. pneumoniae*, it has effective immunoprotection against pneumococcal infections while having no disadvantages of conventional vaccines to prevent the pneumococcal infection having low immunogenicity or not providing protection against all serotypes of streptoccccus.

The invention claimed is:

1. A method for immunizing a human or animal against pneumococcal infections, comprising by administering a vaccine comprising a purified attenuated $ClpP^-$ (Caseinolytic protease $P^-$) mutant of *S. pneumoniae* in an immunologically effective amount to the human or animal, wherein the $ClpP^-$ mutant of *S. pneumoniae* is a mutant where nucleotides at positions 206 to 300 of SEQ ID NO. 2 have been deleted.

* * * * *

SEQUENCE LISTING

```
<160> NUMBER OF SEQ ID NOS: 17

<210> SEQ ID NO 1
<211> LENGTH: 11402
<212> TYPE: DNA
<213> ORGANISM: Streptococcus pneumoniae
<220> FEATURE:
<223> OTHER INFORMATION: R6 section 59 of 184 of genome

<400> SEQUENCE: 1

ttatactatc attgtaagga ggaaatcatg taccatataa aagaagctgc gcagctttca      60

ggtgtctctg tcaagaccct gccctgcatc actatgacaa gataggactc ttggtcccct     120

taaagtcgga aaacggctat cgaacctata gtcaagagga tttggaacgc cttcaggtca     180
```

```
ttctttacta caaatatcta ggcttttctt tagagaaaat agcagagctg ttaaaggaag    240
aaaggacaga tttattgccc catttaacta ggcagttgga ctatctaact cgcgaaaggc    300
aacatctgga taccttgatt tccaccttgc aaaaaactat tcaagaacaa aaaggagaaa    360
gaaaaatgac cattgaggaa aaattcacgg gatttagcta tcaagacaat caaaaatacc    420
accaagaagc ggtagagaaa tatggtcaag aagtcatggg acaagcgctc gaacgccaaa    480
aaggtcacga agacgaggct acggccgcct ttaaccaagt ctttcaaact ttggcacaaa    540
atcttcaagt tggtttacct gcaacagcaa ccgaaaacca agagcaagca gccaagctct    600
tgcaagctat tcgcacttat ggatttgact gctctattga ggtattcggt catatcggta    660
aaggttacgt ctacaaccca gagtttaagg aaaatattga caagtttggt tctgaaacag    720
cccagtacac gtcagatgcc attgcggctt acgttcagac aaatgcagaa taaataggct    780
aggaatttcc tagcctattt tttatttcaa atcataaagc cagtcgtcac cgtttttgta    840
gtaaaagaat tcactgagat cttcttctag aaacacacga agcatatcag acatatcatc    900
ggttgcaagt tttagatgag aaagattttc aaagtcctcc caccaaactt tcccttcgtc    960
tgaagactgg agttcaccag taaagtgttc tgtcttgtaa aaaaggacga cataacgata   1020
atccttgtcg tcataccagt ttttgatacc acagagttgg ggtttggaaa tgatcagacc   1080
agtttcttct ttcacttcac gaatgacagc atcgacaaag gattcgccac gttcaacatg   1140
accaccagga aaagtaatgc caggccagtc gggactaact cggtcttgga ccaggatctt   1200
atctccgttt ttaatcatac acatgttaac aaattcgact gcctctcttc tgttcattct   1260
tcacaacctt taatctttaa tcataatgca gacttcccgc cacccagccg gtacagaggg   1320
cagaagtgat gttaaagcca cccgtgtggg cattgatatc cataacttcg cctgcaaagt   1380
ggaggccagg taccagctta ctttcaaggg ttttaggatt gatttccttg agactgactc   1440
cacccttggt aacaaaggac tttgcaaggg acatttttcc agttacagga attttaagtt   1500
ctttaatgga ctggacaagt tgttctcgtt ccttttcagt cagctgtttg actttttcag   1560
gatatccttg tacaaaaaat tcggccaagc gttctggtaa caaggttttt aaagcgtttt   1620
tcaaggattt ttcccgattt tcttctagaa atgtaaccaa gtccttctca gaaagttgag   1680
gcaaaacatc gagtgagaga acctccccac ctttgacaaa gctagacatg cgtagggcag   1740
caggacctga caaaccaaag tgggtaaaga gtaaatcatg agtgatgaca tgcttaccat   1800
aacttagggt cacatcgtcc agagaaatcc cttgtaaggc tttatgtgga aaatctgtta   1860
ataaaggact ttcagcagcc tcaagatcgg tgatggtatg cttaaaatgg cgagcaatct   1920
cgtgaccaaa gccagtcgaa ccagtcgaag gataagactt accacctgtt gtgacaatga   1980
gtttctcaca agtgaaggtt tgatccgctg acttaaggac aaactggtca tctacttttt   2040
taacagaaac gatttctatt tgagtagcaa cttgaccacc tagttcagtg attttctttt   2100
ccaaagcttc gataatagtc cgagacttgt cactggctgg aaagacgcgt ccgtggtctt   2160
cgaccttaag tttaacacca ttttctgtaa aaaagttgat gatgtcatga ttatcgaact   2220
gggagaaaac actgtaaaga aagcgtccgt ttccaggaat tccagctagc aggttgtcta   2280
agctaccatt gttggtcaca ttgcaacgtc ccccaccagt cccagctaat ttttttccaa   2340
gtttccgatt tttttcgatg aggagggttt tctgtccata aaagctactg gaaatcgtag   2400
ccatcatacc agcaggtccc ccaccgatga caatagtatc aaaatgtttc atagctctat   2460
tgtaccacaa aaaaacaaga gatgatggtc acctcttgtc aagaatgcaa ttaatcaatt   2520
```

-continued

```
tcatagccca tcagcaaacc gccctcttct gcatagaaac tgcagagacc agaggttggt   2580
agaattttaa tatccgcttg tgggaaggtt tcacggattc gctctgagag ctgttgacaa   2640
catttttcgt tattgcgttg ggccatgaca atacggccac cagcatatcc agcttttact   2700
aactcatcat aggcagcttg aactgatttc tttgatcccc ttgctttttg tagcaattcg   2760
agagtcccag tttcactagc ttttccgacc atacgaatgt tgagaaggcc aacgaccgta   2820
ccgataagct tgctcaaacg gccgttcttc accaagttat cgactttggc taggacaaag   2880
agcaacttag ttttttcttg ataggcggtg atagcttcaa ccacttcttc aaaagacaag   2940
ccctggtcaa tcaagtcatt caatttttct acgagtaggt caacttcacc accagcagat   3000
aaactatcaa tcacatgaat cttagtgtca ggatggtctt ccagataaat attctttgct   3060
agttgagcac tattgtgact gccagaaagg gtacctgtga tggttactag gaaaatgttt   3120
ttggcacctt caaatgctcg caaatagtca tctgggcttg gacaagccga ttttgaagct   3180
tctgcagttg catacatggt ttccatcatt tggtcaatat cgagactggc gtcatcaaca   3240
aagacctgat cagctacttg aatggttaag gggacactta caaaggttgt gttaatagct   3300
ggtgttggca gttgacgata atcacaacca gagtcagcaa taatcttcca agtcatagaa   3360
attctccatc tttgtcagtt atacattgac aaaggttctg tctttttta caattatatc   3420
atgaaaaccc ttgaaacaaa agcatcatcc gtctgttgtg acaagtagaa agaaaatgtt   3480
atgtctgaac gtagaatctc tgaaaagtct cttgaaaatc tcagaaaatc aaaccaagaa   3540
tccaatttat taaccagaga agccattgaa acagccctct tgcaactctt ggaaaaaaag   3600
gaactgacca agattagtat ttctgaattg gtcaaacgtg caggtgtttc gcgtgcggcc   3660
ttttatcgca attatgactc caaagaggaa attttagaga gcgtctttaa acgaactgtc   3720
cacaatatta tggaacagct gcatcattac gatttaaaga cagaccttta tttggtttgg   3780
gttcaccttt tccgggaggc cagaaaggaa gctagagtaa ttcaattggc cttggattac   3840
catctggaaa aatctttgt ccaagccatg caggaatttc tagaaaaata ccatgggaaa   3900
tcaaaaggtg tcagctctta tcttcattcc ttctggagct cagccatcgt ctctgtcctt   3960
ctaaaatgga tcaaggatgg catgaaggta ccagctgaaa agattgcaga tttaggttta   4020
ccatttttta aaaaatagag aaaaaggaga aaagagatga ctgaaaaaag actggcctgg   4080
gatgagtatt ttgcagccca agctctacta attgcgaatc gttccacttg taaacgtgct   4140
aaagtgggcg cgattctggt aaaagataat aaggttattt ccactggtta caatggttcg   4200
gtgtcaggga ctgagcattg tattgatcac gaatgtttgg tcattgaagg ccactgcgtt   4260
cgcacccttc acgctgaggt caatgctatc cttcaaggtg ctgagcgtgg tgttcccaaa   4320
ggctttacag cctatgtaac ccattttcct tgtctcaact gtacaaaaca attgcttcag   4380
gtcggctgca agcgcgtggt ttatatcaac cagtaccgaa tggacgacta cgcccaatac   4440
ctttatcaag aaaaagggac agaattgacc catttaccac ttgagacagt acagacagct   4500
cttaaagagg ctgatctaat gtaaaaatta tcaaaaataa atggtttaga aagattttta   4560
aaccgttttt tggtataata agaagaataa attgaaagaa ggaattccaa aaatgggaaa   4620
aattgaagtt attaatcacc cactgattca acacaaattg tcaatcttgc gtcgtacaga   4680
tacttctaca aaagcttttc gtgagctagt agatgagatt gcaatgttga tggggtatga   4740
agtacttcgt gatcttccac tagaagatgt ggaaatcgaa acaccaatta caaaaacagt   4800
tcaaaaacaa ttggcaggta agaaattggc catcgtccca atcttgcgtg caggtatcgg   4860
gatggttgat ggtctcttga gcttggttcc agctgctaaa gttggccaca tcggtatgta   4920
```

```
ccgtgatgaa gaaacacttc aaccagttga atacttggtg aaattgcctg aggacattga   4980
ccaacgtcaa atttttgtag tagacccaat gttggcaaca ggtggctcag caatcttggc   5040
tgttgattct cttaaaaaac gtggcgcatc aaatatcaaa tttgtctgcc ttgtatctgc   5100
tccagagggt gtaaaagccc ttcaagaagc tcatccagat gtagaaatct ttacagcagc   5160
cttggatgaa cgtttgaacg aacacggtta tatcgttcca ggtcttggag atgctggaga   5220
ccgcttgttc ggtacaaaat aagatcgaaa agaagaatga cttggaaaag tatttccagt   5280
cacgaaagga ggttgggttt ttgtttctgt ctaatgaaag cagagcaaaa atttgacctt   5340
ttttgaccaa gatattataa tagtcttatc ttcagtcatt tgaccaacaa aattaaaact   5400
caaaaggaga aatgaatgat tcctgtagtt attgaacaaa caagccgtgg agaacgttct   5460
tacgatattt actcacgtct tctcaaagac cgcatcatta tgctgacagg tccggttgaa   5520
gacaatatgg ctaactctgt tattgcccaa ctgcttttct tggatgccca agatagtaca   5580
aaagatattt acctttatgt caatacacca ggtggttctg tttcagctgg tttggcaatc   5640
gtagatacca tgaactttat caaggcagat gtccaaacca ttgttatggg aatggctgca   5700
tctatgggaa cagtcatcgc atcaagtgga gcaaaaggca aacgtttcat gcttccaaat   5760
gctgaataca tgattcacca accaatgggc ggtacaggtg gtggtaccca acaaactgat   5820
atggctatcg ctgcagaaca cttgctcaaa actcgtaata ccttggaaaa aatcttggct   5880
gaaaattcag gtcagtcaat ggaaaaagtc catgcagatg cagaacgtga taactggatg   5940
agcgcccagg aaacacttga atatggcttt attgatgaaa ttatggccaa caattcattg   6000
aactaatgat gatagaaggc aaactcgact gggtttgctt tttttggtat aatagggaga   6060
gatttcttag aaagaggatt tatcatgttt gaaaaagtca atcgctctgg cttgattatc   6120
tatctttact ataatcgtga tgccaaaaaa ctgcaggatt atggagatat tacctatcat   6180
tccaagaaac atcgttactt acaactctat gttccaactc aagaagtgga gcaattggtc   6240
ggacgcttga gcaaggaaaa atttattaaa aaagttaggg tttgtcatat ccaagagttg   6300
gaaacaccct ttgtgggcaa tctttatcga taggaaaacg ctatcatcga aaaagttcaa   6360
ggaaaacatt gacaattttc tgataattcg gtatattctt aacagactat ttaagaaata   6420
aggagacaaa aaagatgaag aaaaaatttg ccctatcgtt tgtggcgctt gcaagtgtag   6480
cacttcttgc agcctgtgga gaagtgaagt ctggagcagt caacactgct ggtaactcag   6540
tagaggaaaa gacaattaaa atcgggttta actttgaaga atcaggttct ttagctgcat   6600
acggaacagc tgaacaaaaa ggtgcccaat tggctgttga tgaaatcaat gccgcaggtg   6660
gtatcgatgg aaaacaaatc gaagtagtcg ataaagataa taagtctgaa acagctgagg   6720
ctgcttcagt tacaactaac cttgtaaccc aatctaaagt atcagcagtc gtaggacctg   6780
cgacatctgg tgcgactgca gctgcggtag cgaacgctac aaaagcaggt gttccattga   6840
tctcaccaag tgcgactcaa gatggattga ctaaaggtca agattacctc tttattggaa   6900
ctttccaaga tagcttccaa ggaaaaatta tctcaaacta tgtttctgaa aaattaaatg   6960
ctaagaaagt tgttctttac actgacaatg ccagtgacta tgctaaaggg attgccaaat   7020
ctttccgcga gtcatacaag ggtgaaatcg ttgcagatga aactttcgta gcaggtgaca   7080
cagacttcca agcagccctt acaaaaatga aagggaaaga ctttgatgct atcgttgttc   7140
ctggttacta taatgaggct ggtaagattg taaaccaagc gcgtggtatg ggaattgaca   7200
aaccaatcgt tggtggtgat ggattcaacg gtgaggagtt tgtacaacaa gcaactgctg   7260
```

-continued

```
aaaaagcatc aaacatctac tttatctcag gcttctcaac tactgtagaa gtttcagcta   7320
aagctaaagc cttccttgac gcttaccgtg ctaagtacaa tgaagagcct tcaacatttg   7380
cagccttggc ttatgattca gttcaccttg tagcaaacgc agcaaaaggt gctaaaaatt   7440
caggtgaaat caagaataac cttgctaaaa caaaagattt tgaaggtgta actggtcaaa   7500
caagcttcga tgcagaccac aacacagtca aaactgctta catgatgacc atgaacaatg   7560
gtaaagttga agcagcagaa gttgtaaaac cataatagaa aaatgttgaa atagggaatg   7620
agcctttgac tcactccctg tttcgatatt taatactctt cgaaaatctc ttcaaactgc   7680
gtcaacgtcg ccttggatta tatatgtgac tgacttcgtc agtcttatct acaacctcaa   7740
agcagtgctt tgagcaacct gcggctagtt tcctagtttg ctctttgatt ttcattgagt   7800
ataagaacct atcaaaaagt gagggaaaac cctcggaatt ataaatagaa agagtgaatc   7860
ttatgctcca acaactcgta aatggtttga ttctaggtag tgtttacgcg ctgttagccc   7920
taggatatac catggtttac ggaattatca agctcatcaa cttcgcccat ggtgatattt   7980
atatgatggg agcctttatc ggttatttct tgatcaattc tttccaaatg aatttctttg   8040
tagcgcttat tgtagctatg ctagcgacag ctattcttgg tgtcgtgatt gagtttcttg   8100
cttaccgacc tttgcgccac tctactcgta ttgctgtttt gattacggct attggggttt   8160
ctttcctatt ggagtatgga atggtctatc tggttggtgc caatacccgt gccttccctc   8220
aagcgattca aacagttcga tatgatttgg gaccaattag cttaacaaat gtgcagttaa   8280
tgattttggg catttccttg attttgatga ttttgttaca agtcattgtc caaaagacta   8340
agatggggaa agccatgcgt gcagtatcag tagatagcga cgcggcgcaa ttgatgggga   8400
tcaatgtaaa ccgtacgatt agctttacct tcgctttggg ttctgctctt gcgggtgcgg   8460
ctggtgttct gattgctctt tattataact ctcttgagcc tttgatgggg gttactccag   8520
gtcttaaatc tttcgttgcc gcagtacttg gtggtatcgg aattattcct ggtgcggctc   8580
ttggtggctt tgtgattggt ctattggaaa cctttgcgac agcctttggg atgtcagatt   8640
tccgtgatgc cattgtttat ggaatcttgt tgttgatctt gattgtccgc ccagctggta   8700
tccttggtaa gaatgtgaaa gagaaggtgt aaacgatgaa ggaaaattta aaagttaata   8760
ttctatggtt actccttttg ttagctggct atagcttgat tagtgtactg gtttcagtcg   8820
gagtacttaa tctattctat gtacagattt tacaacaaat tggaattaat attattttgg   8880
ctgttggtct caacttaatc gttggttttt caggacaatt ttcacttggt catgctggtt   8940
tcatggcgat tggtgcctat gccgcagcta ttattggttc taaatcacca acctacggtg   9000
ccttctttgg agctatgctt gtaggggctt tgctttcagg agcagttgcc ttacttgtcg   9060
gcattccaac cttgcgcttg aagggggact atcttgcggt agcaactctg ggtgtttctg   9120
aaattatccg tatctttatc atcaatggtg gaagtcttac aaatggtgcg gcaggtatct   9180
tagggattcc taactttaca acttggcaaa tggtttactt ctttgtcgtg attacaacca   9240
ttgcaacctt gaacttcttg cgtagcccaa ttggccgttc aaccctctct gttcgtgaag   9300
atgaaatcgc tgctgagtca gttggggtta atacgactaa aattaaaatc atcgcttttg   9360
tctttggtgc cattactgca agtattgctg ggtcacttca ggcaggattt atcgggtctg   9420
ttgtaccgaa agattacacc ttcatcaact caatcaacgt tttgattatt gttgtatttg   9480
gtggactcgg ttccattaca ggtgcgattg tttcggctat tgttctggga attttgaata   9540
tgcttctcca agatgttgct agtgtgcgta tgattattta cgctttggcc ttggtattgg   9600
taatgatttt cagaccaggt ggactccttg gaacgtggga actgagccta tcacgtttct   9660
```

```
ttaaaaaatc taagaaggag gaacaaaact aatggcatta cttgaagtaa aacagttaac   9720

caaacatttt ggtggtctaa cagctgttgg agatgtgact cttgaattga acgaagggga   9780

actggttgga ttaatcggtc caaacggagc tgggaaaacc accctttca accttttgac   9840

cggtgtttat gaaccaagcg agggaacagt aaccctagat ggtcaccttt tgaatgggaa   9900

atcaccttat aagattgcct ctttgggact tggacgtact ttccaaaata tccgtctctt   9960

taaagattta acagttttag acaatgtttt gattgctttt ggaaaccatc acaaacaaca  10020

tgtttttact agtttcttac gcttaccagc tttttacaag agtgaaaaag aattaaaggc  10080

taaagctttg gaattgttga aatctttga tttagatggt gatgcagaga ctcttgctaa  10140

aaatctttcc tacggacaac aacgtcgttt ggaaattgtt cgtgcccttg ctacggaacc  10200

taaaattctc ttcttagatg aaccagcagc aggtatgaac ccacaggaaa cagccgaatt  10260

gactgagtta attcgtcgta tcaaagatga atttaagatt acaatcatgt tgattgaaca  10320

cgatatgaat ctggtcatgg aagtaacaga acgtatctac gtacttgaat atggccgttt  10380

aattgctcaa ggaactccag acgaaattaa gaccaataaa cgcgttatcg aagcttatct  10440

aggaggtgaa gcctaatgtc tgtgttaaaa gttgaaaatc tttctgtgca ttacggtatg  10500

atccaagcag tccgtgatgt aagctttgaa gttaatgaag gagaagttgt ttcccttatc  10560

ggtgccaacg gtgcaggtaa gacaactatt cttcgcacct tgtcaggttt ggttcgacca  10620

agttcaggaa agattgaatt tttaggtcaa gaaatccaaa aaatgccagc tcagaaaatt  10680

gtggcaggtg gtctttcaca agttccagaa ggacgccacg tctttcctgg cttgactgtt  10740

atggaaaatc ttgaaatggg agctttctta aagaaaaatc gtgaagaaaa tcaagctaac  10800

ttgaagaagg ttttctcacg ctttcctcgt cttgaagaac gtaagaacca agatgcagct  10860

actctttcag gaggggaaca acaaatgctt gccatgggac gcgctcttat gtcaacacca  10920

aaacttcttc ttttagatga accatcaatg ggacttgccc caatcttcat ccaagagatt  10980

tttgatatca ttcaagatat tcagaagcaa ggaacaaccg tcctcttgat tgaacaaaat  11040

gccaataaag cacttgcaat ctctgaccga ggatatgtac tggaaacagg gaaaatcgtc  11100

ctatcaggaa caggaaaaga actcgcctca tcagaagaag tcagaaaagc atatctaggt  11160

ggctaaaaca atccagtgga ttgttttagt cggcagatga agattacgaa gtaatcatca  11220

ttatagtctg ggagactagt ttaggttgca gataaagatt gcgaagcaat catcaaatcc  11280

agaggattgt tttagccggc agatggagat tacgaagtaa tcatcaatat agtcctgggg  11340

acctttttag tcggtggata gagattgcaa acaaatatgc atctacattg aaagcttaat  11400

tt                                                                 11402
```

```
<210> SEQ ID NO 2
<211> LENGTH: 591
<212> TYPE: DNA
<213> ORGANISM: Streptococcus pneumoniae
<220> FEATURE:
<223> OTHER INFORMATION: R6 positions 5416 to 6006 of section 59 of 184
      of genome

<400> SEQUENCE: 2

atgattcctg tagttattga acaaacaagc cgtggagaac gttcttacga tatttactca     60

cgtcttctca aagaccgcat cattatgctg acaggtccgg ttgaagacaa tatggctaac    120

tctgttattg cccaactgct tttcttggat gcccaagata gtacaaaaga tatttacctt    180

tatgtcaata caccaggtgg ttctgtttca gctggtttgg caatcgtaga taccatgaac    240
```

tttatcaagg cagatgtcca aaccattgtt atgggaatgg ctgcatctat gggaacagtc 300
atcgcatcaa gtggagcaaa aggcaaacgt ttcatgcttc caaatgctga atacatgatt 360
caccaaccaa tgggcggtac aggtggtggt acccaacaaa ctgatatggc tatcgctgca 420
gaacacttgc tcaaaactcg taataccttg gaaaaaatct tggctgaaaa ttcaggtcag 480
tcaatggaaa aagtccatgc agatgcagaa cgtgataact ggatgagcgc ccaggaaaca 540
cttgaatatg gctttattga tgaaattatg gccaacaatt cattgaacta a 591

<210> SEQ ID NO 3
<211> LENGTH: 20
<212> TYPE: DNA
<213> ORGANISM: Artificial Sequence
<220> FEATURE:
<223> OTHER INFORMATION: 16S rRNA specific primer

<400> SEQUENCE: 3
ggtgagtaac gcgtaggtaa 20

<210> SEQ ID NO 4
<211> LENGTH: 20
<212> TYPE: DNA
<213> ORGANISM: Artificial Sequence
<220> FEATURE:
<223> OTHER INFORMATION: 16S rRNA specific primer

<400> SEQUENCE: 4
acgatccgaa aaccttcttc 20

<210> SEQ ID NO 5
<211> LENGTH: 22
<212> TYPE: DNA
<213> ORGANISM: Artificial Sequence
<220> FEATURE:
<223> OTHER INFORMATION: prs3 from E. coli.

<400> SEQUENCE: 5
ccgggcccaa aatttgtttg at 22

<210> SEQ ID NO 6
<211> LENGTH: 22
<212> TYPE: DNA
<213> ORGANISM: Artificial Sequence
<220> FEATURE:
<223> OTHER INFORMATION: prs4 from E. Coli.

<400> SEQUENCE: 6
agtcggcagc gactcataga at 22

<210> SEQ ID NO 7
<211> LENGTH: 25
<212> TYPE: DNA
<213> ORGANISM: Artificial Sequence
<220> FEATURE:
<223> OTHER INFORMATION: hlp3 from Streptococcus pneumoniae

<400> SEQUENCE: 7
cggtaccatg aacaataatt ttaac 25

<210> SEQ ID NO 8
<211> LENGTH: 43
<212> TYPE: DNA
<213> ORGANISM: Artificial Sequence
<220> FEATURE:

<223> OTHER INFORMATION: hlp1 from Streptococcus pneumoniae

<400> SEQUENCE: 8
atcaaacaaa ttttgggccc ggtcagatgt ttcttgaatt tcc 43

<210> SEQ ID NO 9
<211> LENGTH: 43
<212> TYPE: DNA
<213> ORGANISM: Artificial Sequence
<220> FEATURE:
<223> OTHER INFORMATION: hlp2 from Streptococcus pneumoniae

<400> SEQUENCE: 9
attctatgag tcgctgccga ctgttctaga tgatggtcgt ttg 43

<210> SEQ ID NO 10
<211> LENGTH: 31
<212> TYPE: DNA
<213> ORGANISM: Artificial Sequence
<220> FEATURE:
<223> OTHER INFORMATION: hlp4 from Streptococcus pneumoniae

<400> SEQUENCE: 10
ggccgagctc ttagactttc tcacgaataa c 31

<210> SEQ ID NO 11
<211> LENGTH: 24
<212> TYPE: DNA
<213> ORGANISM: Artificial Sequence
<220> FEATURE:
<223> OTHER INFORMATION: hpp3 from Streptococcus pneumoniae

<400> SEQUENCE: 11
cgaattcatg attcctgtag ttat 24

<210> SEQ ID NO 12
<211> LENGTH: 43
<212> TYPE: DNA
<213> ORGANISM: Artificial Sequence
<220> FEATURE:
<223> OTHER INFORMATION: hpp11 from Streptococcus pneumoniae

<400> SEQUENCE: 12
attctatgag tcgctgccga ctcagaacca cctggtgtat tga 43

<210> SEQ ID NO 13
<211> LENGTH: 43
<212> TYPE: DNA
<213> ORGANISM: Artificial Sequence
<220> FEATURE:
<223> OTHER INFORMATION: hpp10 from Streptococcus pneumoniae

<400> SEQUENCE: 13
atcaaacaaa ttttgggccc ggatcgcatc aagtggagca aaa 43

<210> SEQ ID NO 14
<211> LENGTH: 26
<212> TYPE: DNA
<213> ORGANISM: Artificial Sequence
<220> FEATURE:
<223> OTHER INFORMATION: hpp6 from Streptococcus pneumoniae

<400> SEQUENCE: 14
cgagctctta gttcaatgaa ttgttg 26

```
<210> SEQ ID NO 15
<211> LENGTH: 27
<212> TYPE: DNA
<213> ORGANISM: Artificial Sequence
<220> FEATURE:
<223> OTHER INFORMATION: Streptococcus pneumoniae Clp family

<400> SEQUENCE: 15

gatgaayaay aayttyaaya ayttyaa                                    27


<210> SEQ ID NO 16
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: 2nd ATP binding region for Streptococcus
      pneumoniae Clp family; in each occurrence, n is a, c, g, or t

<400> SEQUENCE: 16

gtyttnccnc anccngyngg                                            20


<210> SEQ ID NO 17
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: CtsR repressor binding sequence in upstream of
      ClpL; in each occurrence, n is a, c, g, or t

<400> SEQUENCE: 17

gtcaaananr gtcaaa                                                16
```